United States Patent
Eisen et al.

(10) Patent No.: US 8,868,149 B2
(45) Date of Patent: Oct. 21, 2014

(54) PHOTOPLETHYSMOGRAPHY DEVICE AND METHOD

(71) Applicants: Leon Eisen, Ashdod (IL); Alexander Kamisnky, Rehovot (IL); Ilya Fine, Rehovot (IL)

(72) Inventors: Leon Eisen, Ashdod (IL); Alexander Kamisnky, Rehovot (IL); Ilya Fine, Rehovot (IL)

(73) Assignee: Oxitone Medical Ltd., Ashkelon (IL)

( * ) Notice: Subject to any disclaimer, the term of this patent is extended or adjusted under 35 U.S.C. 154(b) by 0 days.

(21) Appl. No.: 13/653,233

(22) Filed: Oct. 16, 2012

(65) Prior Publication Data

US 2013/0131475 A1  May 23, 2013

Related U.S. Application Data

(63) Continuation-in-part of application No. 12/847,048, filed on Jul. 30, 2010, now abandoned, and a continuation-in-part of application No. PCT/IL2010/000616, filed on Aug. 1, 2010.

(60) Provisional application No. 61/229,741, filed on Jul. 30, 2009.

(51) Int. Cl.
  *A61B 5/00* (2006.01)
  *A61B 5/145* (2006.01)
  *A61B 5/1455* (2006.01)
  *A61B 5/024* (2006.01)

(52) U.S. Cl.
  CPC ........... *A61B 5/14552* (2013.01); *A61B 5/7207* (2013.01); *A61B 5/681* (2013.01); *A61B 5/14546* (2013.01); *A61B 5/7285* (2013.01); *A61B 5/14551* (2013.01); *A61B 5/7257* (2013.01); *A61B 5/7246* (2013.01); *A61B 5/02416* (2013.01)
  USPC ........................................................ 600/324

(58) Field of Classification Search
  USPC ........................................................ 600/324
  See application file for complete search history.

(56) References Cited

U.S. PATENT DOCUMENTS

| | | | |
|---|---|---|---|
| 5,284,149 A * | 2/1994 | Dhadwal et al. | 600/476 |
| 5,598,841 A * | 2/1997 | Taniji et al. | 600/342 |
| 6,754,515 B1 * | 6/2004 | Pologe | 600/322 |
| 7,254,432 B2 * | 8/2007 | Fine | 600/335 |
| 2004/0260165 A1 * | 12/2004 | Cho et al. | 600/365 |
| 2006/0063995 A1 * | 3/2006 | Yodh et al. | 600/323 |
| 2009/0209834 A1 * | 8/2009 | Fine | 600/316 |

* cited by examiner

*Primary Examiner* — Clayton E Laballe
*Assistant Examiner* — Linda B Smith
(74) *Attorney, Agent, or Firm* — Marc Van Dyke; 4$^{th}$ Dimension IP

(57) ABSTRACT

A system and method for measuring one or more light-absorption related blood analyte concentration parameters of a mammalian subject, is disclosed. In some embodiments, the system comprises: a) a photoplethysmography (PPG) device configured to effect a PPG measurement by illuminating skin of the subject with at least two distinct wavelengths of light and determining relative absorbance at each of the wavelengths; b) a dynamic light scattering measurement (DLS) device configured to effect a DLS measurement of the subject to rheologically measure a pulse parameter of the subject; and c) electronic circuitry configured to: i) temporally correlating the results of the PPG and DLS measurements; and ii) accordance with the temporal correlation between the PPG and DLS measurements, assessing value(s) of the one or more light-absorption related blood analyte concentration parameter(s).

1 Claim, 27 Drawing Sheets

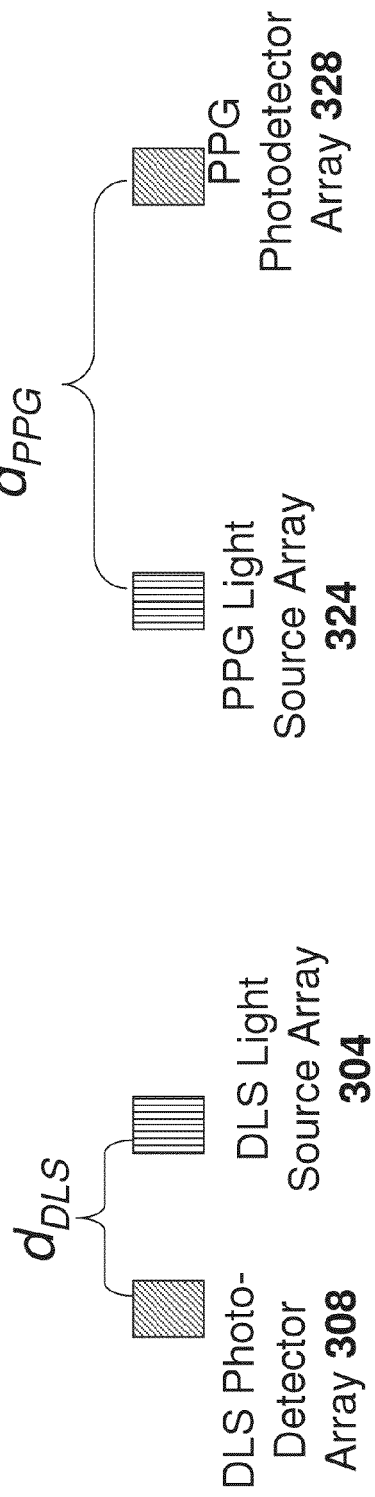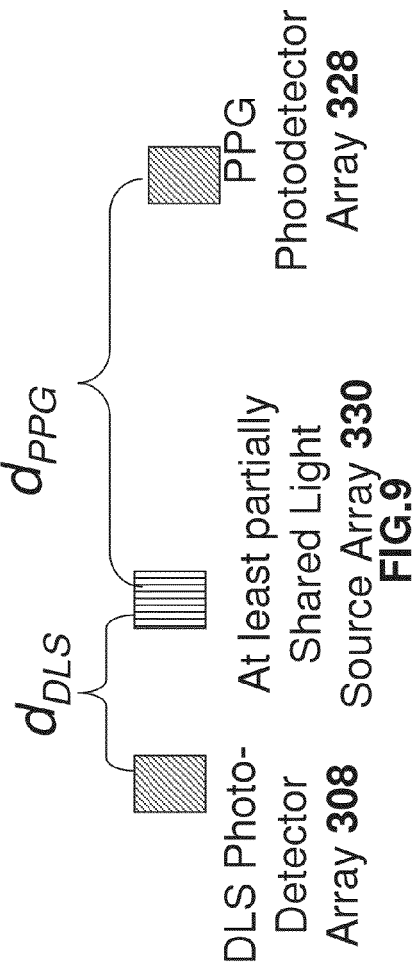
FIG. 9

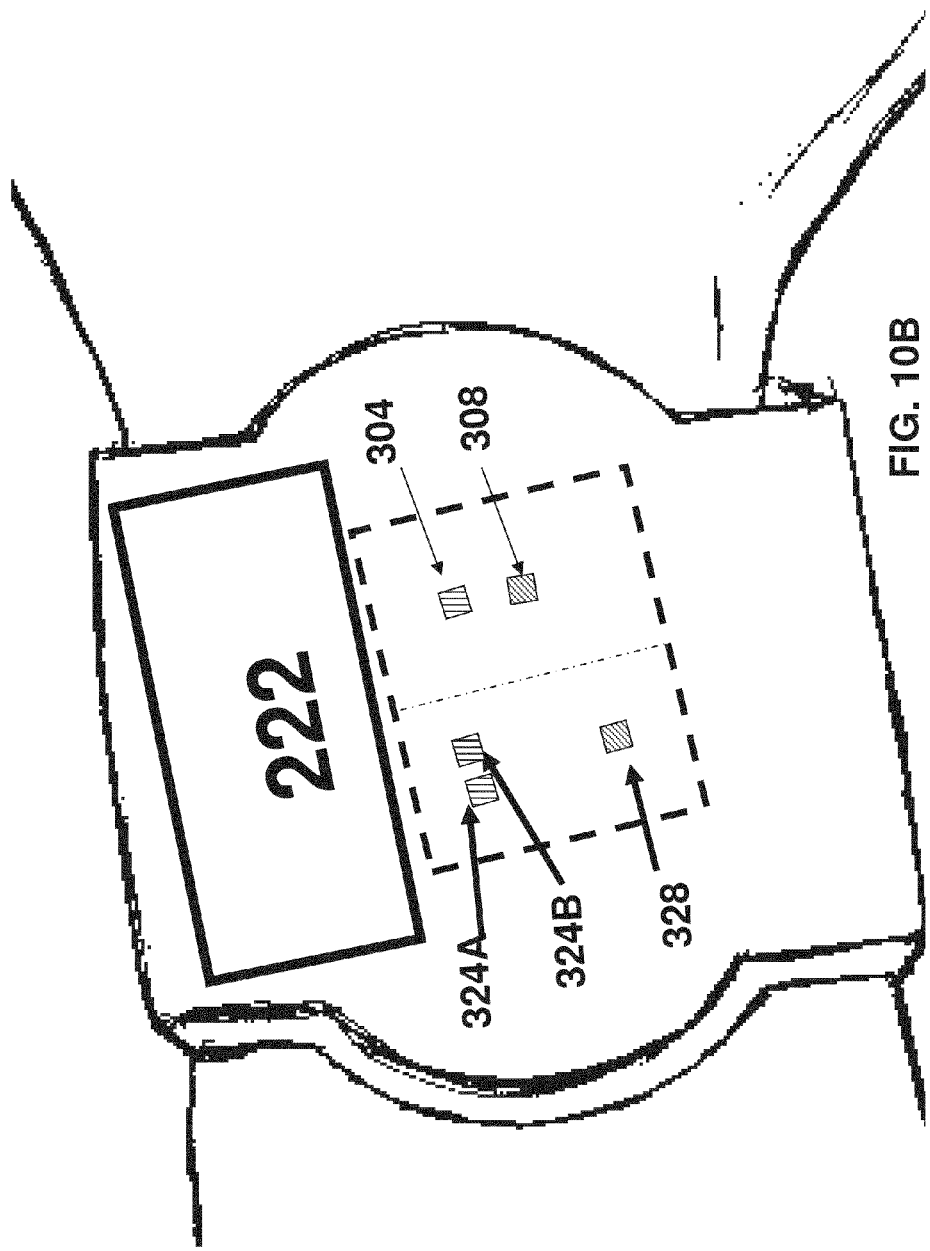

CONVENTIONAL TECHNIQUE

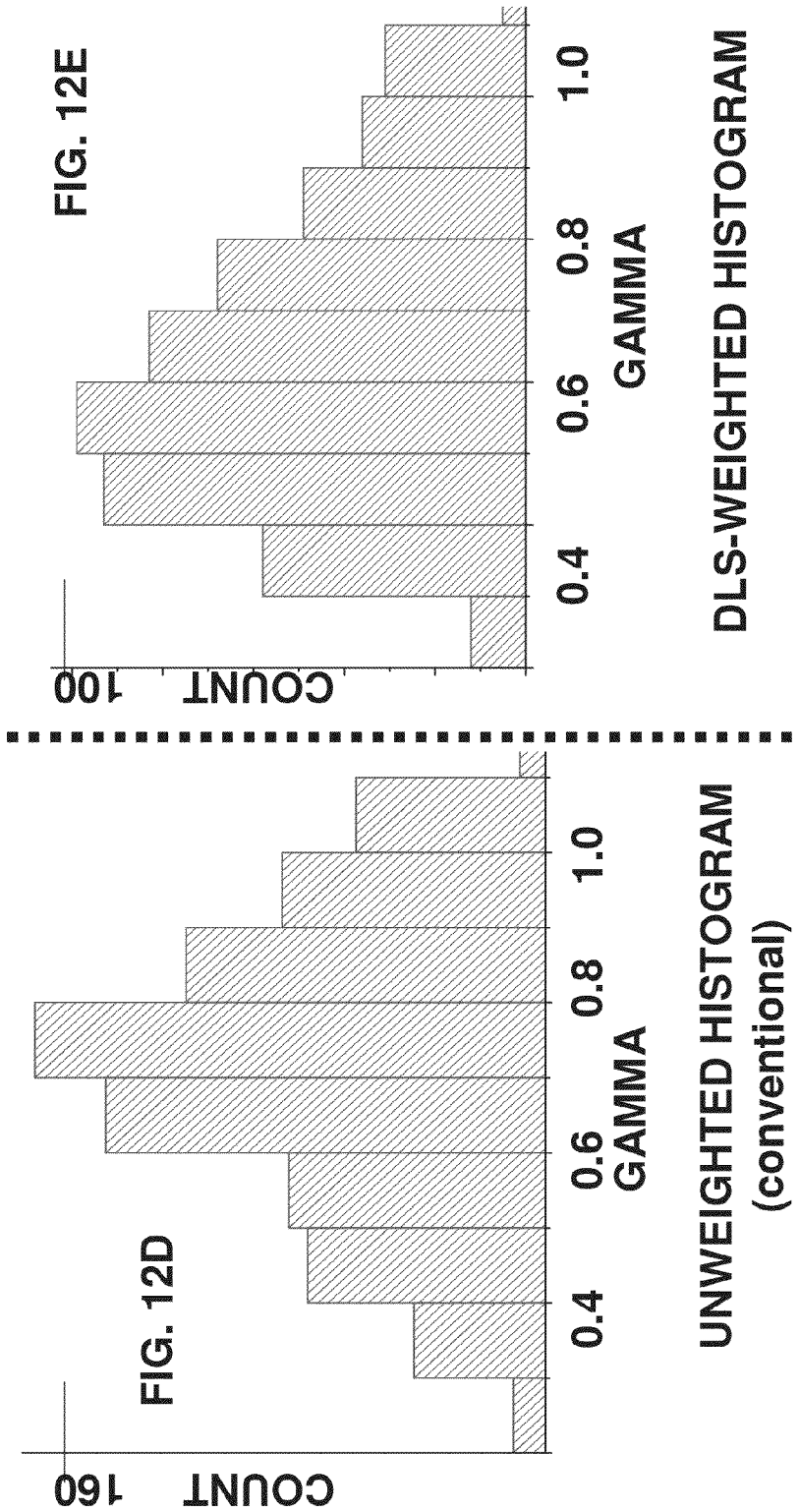

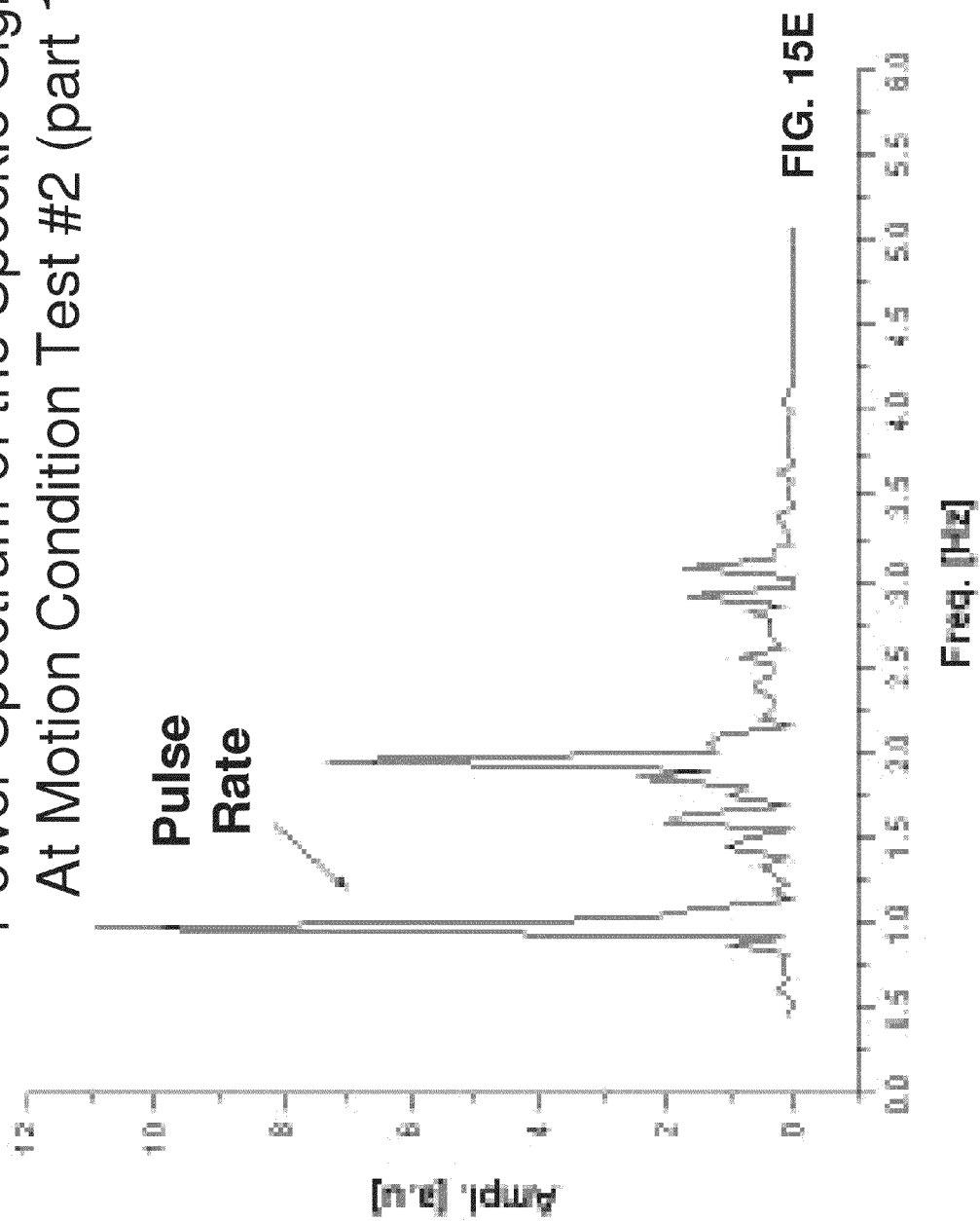

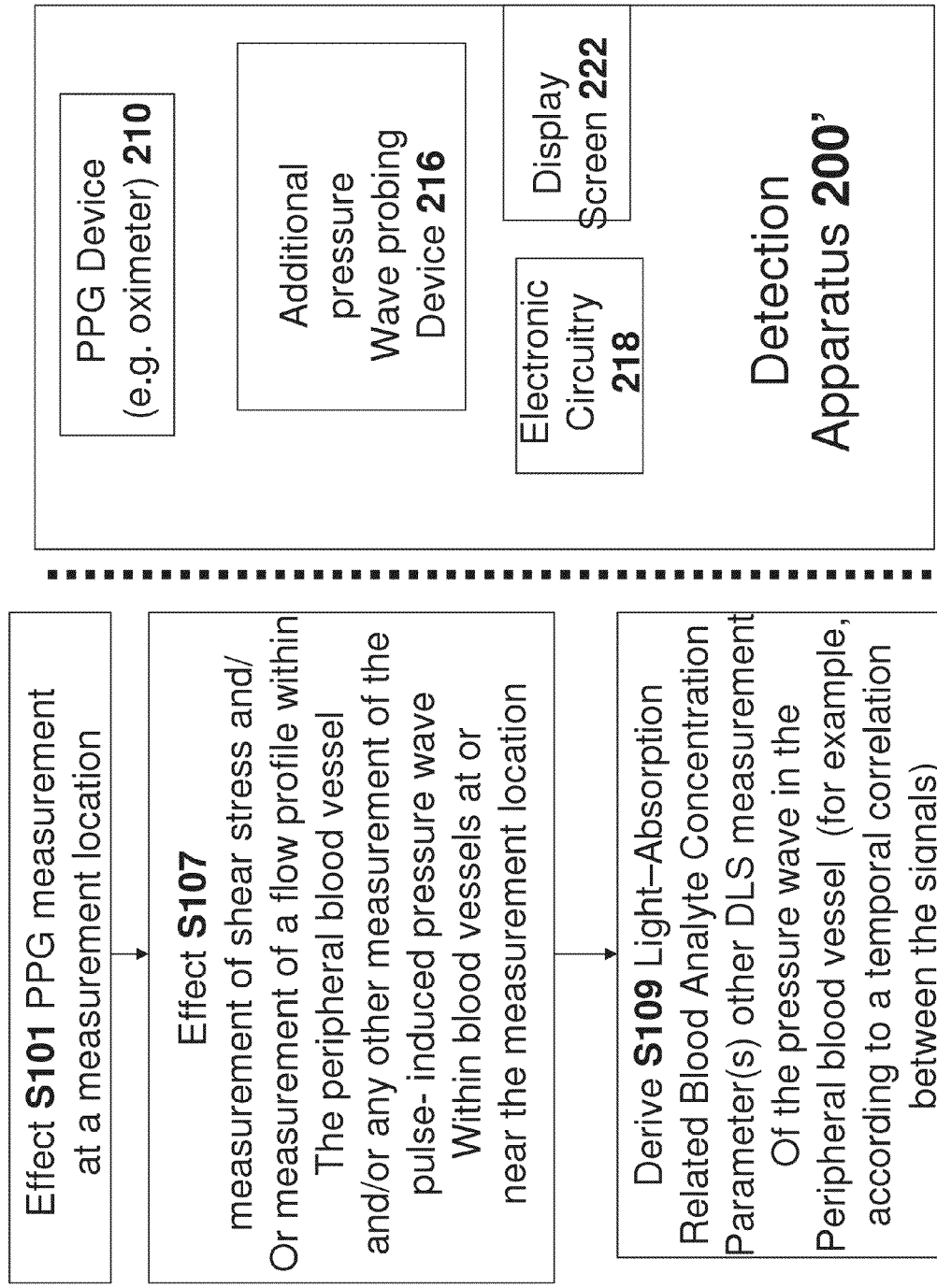

PHOTOPLETHYSMOGRAPHY DEVICE AND METHOD

RELATED APPLICATION INFORMATION

This application is a continuation-in-part of U.S. Nonprovisional application Ser. No. 12/847,048 filed on Jul. 30, 2010, which is incorporated herein by reference in its entirety. This application is a continuation-in-part of PCT/IL2010/000616 filed on Aug. 1, 2010 which is incorporated herein by reference in its entirety. This application claims priority from U.S. Provisional Application Ser. No. 61/229,741 filed on Jul. 30, 2009.

FIELD OF THE INVENTION

The present invention relates to a system and method for in vivo measurement measurements of blood parameters (for example, a light-absorption related blood analyte concentration parameter such as blood oxygen saturation) according to one or more detected biological light response signals.

BACKGROUND AND RELATED ART

Pulse Oximetry

Pulse oximeter devices based on photoplethysmography techniques are well known in the art. Wikipedia defines pulse oximetry as "a non-invasive method allowing the monitoring of the oxygenation of a patient's hemoglobin." The subject's skin at a 'measurement location' is illuminated with two distinct wavelengths of light and the relative absorbance at each of the wavelengths is determined.

Wikipedia describes usage of pulse oximeter devices as follows:

A sensor is placed on a thin part of the patient's body, usually a fingertip or earlobe, or in the case of a neonate, across a foot, and a light containing both red and infrared wavelengths is passed from one side to the other. Changing absorbance of each of the two wavelengths is measured, allowing determination of the absorbances due to the pulsing arterial blood alone, excluding venous blood, skin, bone, muscle, fat, and (in most cases) fingernail polish. Based upon the ratio of changing absorbance of the red and infrared light caused by the difference in color between oxygen-bound (bright red) and oxygen-unbound (dark red or blue, in severe cases) blood hemoglobin, a measure of oxygenation (the percent of hemoglobin molecules bound with oxygen molecules) can be made.

FIG. 1 illustrates extinction curves for both hemoglobin and oxihemoglobin. As is evident from FIG. 1, at a wavelength in the visible red spectrum (for example, at 660 nm), the extinction coefficient of hemoglobin exceeds the extinction coefficient of oxihemoglobin. At a wavelength in the near infrared spectrum (for example, at 940 nm), the extinction coefficient of oxihemoglobin exceeds the extinction coefficient of hemoglobin.

"Pulse Oximetry" by Dr. V. Kamat *Indian J. Anesth.* 2002; 46(4), 261-268 Kamat provides an overview of known features of Pulse Oximetry. The Kamat document describes various features of Pulse Oximetry as follows:

"The pulse oximeter combines the two technologies of spectrophotometry (which measures hemoglobin oxygen saturation) and optical plethysmography (which measures pulsatile changes in arterial blood volume at the sensor site) . . . .

Detection of oxygen saturation of hemoglobin by spectrophotometry is based on Beer-Lambert law, which relates the concentration of a solute to the intensity of light transmitted through a solution. In order to estimate the concentration of a light absorbing substance in a clear solution from the intensity of light transmitted through the solution, one needs to know the intensity and wavelength of incident light, the transmission path length, and absorbance of the substance at a specific wavelength (the extinction coefficient) . . . .

Modern pulse oximeters consist of a peripheral probe together with a microprocessor unit displaying a waveform, the oxygen saturation and the pulse rate. The probe is placed on the digit, earlobe or nose. Within the probe are two LEDs, one in the visible red spectrum (660 nm) and the other in the infrared spectrum (940 nm). The beams of light pass through the tissues to the photo detector. During passage through the tissues some light is absorbed by blood and soft tissues depending on the concentration of hemoglobin. The amount of light absorption at each frequency depends upon the degree of oxygenation of hemoglobin within the tissues.

There are several technical problems in accurately estimating oxygen saturation by this method, as scatter, reflection and absorbance of light by other tissue and blood components could confound the values. The system needs to isolate absorbance of arterial blood from venous blood, connective tissue and other extraneous matter. This can be accomplished easily as arterial blood is pulsatile unlike other tissue. Thus the pulse added signal can be distinguished from nonpulsatile signal by filtering the extraneous .noise.' . . . .

The microprocessor can select out the absorbance of the pulsatile fraction of the blood i.e. that due to arterial blood (AC), from the constant absorbance by nonpulsatile venous or capillary blood and other tissue pigments (DC), thus eliminating the effect of tissue absorbance to measure the oxygen saturation of arterial blood.

The pulsatile expansion of the arteriolar bed produces an increase in path length thereby increasing the absorbance. All pulse oximeters assume that the only pulsatile absorbance between the light source and the photodetector is that of arterial blood. The microprocessor first determines the AC component of absorbance at each wavelength and divides this by the corresponding DC component. From the proportions of light absorbed by each component at the two frequencies it then calculates the ratio (R) of the "pulse-added" absorbance.

$$R = \frac{AC_{660}/DC_{660}}{AC_{940}/DC_{940}},$$

The AC fluctuation is due to the pulsatile expansion of the arteriolar bed due to the volume increase in arterial blood in the vasculature. In most conventional pulse oximeters, in order to measure the AC fluctuation, measurements are taken at different times including a first measurement time at or near a 'peak' and at a second measurement time at or near a 'valley' (see FIG. 2). The 'peak' and 'valley' measurements are compared in order to compute the aforementioned R parameter (often referred to as γ in the literature).

Because difference in measured light absorption at the two times is due primarily to the fact that the light needs to traverse a different volume of blood at the two measurement times, the measurement provided by pulse oximeters is said to be a 'volumetric measurement' descriptive of the differential volumes of blood present at a certain location within the patient's arteriolar bed at different times.

In pulse oximetry, the light absorbance values measured at different times are compared—for example, by comparing (e.g. by computing some sort of difference function to determine the relative magnitudes of the AC and DC components) a first measurement acquired at one of the (i is a positive integer) 'peak times' $t_{peak}{}^i$ with a measurement acquired at one of the measurement acquired at one of the 'valley times' $t_{valley}{}^i$. Because the human pulse is typically on the order of magnitude of one 1 HZ, typically the time differences between these 'pairs of time' (i.e. one peak, one valley) are on the order of magnitude of milliseconds or tens of milliseconds or hundreds of milliseconds. Thus, in most conventional oximeters, light absorbance measurements are acquired at a frequency of around 10-100 of Hz.

Dynamic Light Scattering

Dynamic light scattering is a tool for measuring a variety of blood parameters.

Dynamic light scattering (DLS) is a well-established technique to provide data on the size and shape of particles from temporal speckle analysis. When a coherent light beam (laser beam, for example) is incident on a scattering (rough) surface, a time-dependent fluctuation in the scattering properties of the surface and thus in the intensity of the light scattering (transmission and/or reflection) from the surface is observed. These fluctuations are due to the fact that the particles are undergoing Brownian or regular flow motion and, so, the distance between the particles is randomly changing with time. This scattered light then undergoes either constructive or destructive interference with the light scattered by surrounding particles that results in the random intensity fluctuations. Within these intensity fluctuations information about the time scale of particles movement is contained. The scattered light forms the speckle pattern, being detected in the far diffraction zone. The laser speckle is a random interference pattern produced at the screen or photodetector plane by the coherent light reflected or scattered from different spots on the illuminated surface. If the scattering particles are moving, a time-varying speckle pattern is generated. The intensity variations of this pattern contain information about the scattering particles. The detected signal is amplified and digitized for further analysis by using the autocorrelation function (ACF) technique. The technique is realized either by heterodyne or by a homodyne DLS setup.

As discussed in WO 2008/053474, incorporated herein by reference in its entirety, DLS may be used to probe blood parameters during occlusion (see FIG. 5 of WO 2008/053474 and the accompanying discussion) such that it is possible to derive viscosity and 'scatterer size' (in this case, average size of red blood cell aggregates or Rouleaux).

DLS techniques are not limited to measurements of post-occlusion signals. DLS techniques are also useful for determining a local pulse rate of the subject at the 'measurement site' illuminated by the coherent light according to the local optical properties of the measurement sight. The skilled artisan is referred, for example, to FIG. 9 of WO 2008/053474 and the accompanying discussion.

In contrast to photoplethysmography which is used to measure time-dependent volumetric properties of blood from light intensity measurements descriptive of a transmission optical path length between a light source and a photodetector, DLS techniques are employed to measure time-dependent velocities of scatterers (i.e. red-blood cells or aggregates thereof) suspended within the plasma. In one example, it is possible to analyze rapid fluctuations of the light response signal to determine Brownian velocities of particles during occlusion (see FIG. 5 of WO 2008/053474 and the accompanying discussion). In another example, it is possible to determine a blood velocity changes profile within a blood vessel for the laminar flow of suspended scatterers (i.e. red-blood cells or aggregates thereof). From the flow profile a magnitude of shear forces within the blood vessels can be easily determined.

Both PPG and DLS techniques may be employed to derive blood dynamic parameters from the dynamic response of living tissue to light. However, speckle analysis should entail acquiring measurement data values at a much greater frequency (and comparing/computing functions of these measurement data values) than is needed for photoplethysmography—for example, a frequency of at least 3 kHZ or at least 5 kHZ or at least 10 kHZ. For example, in many implementations, measurement values having 'time gaps' of less than one half of a millisecond are compared to compute the velocity of a scatterer.

One salient feature provided by some embodiments of DLS is the ability to compute a blood rheological parameter according to 'very short time scale trends' (i.e. as opposed to only average values). Thus, one or more DLS measurements may be carried out in accordance with a difference of measurement values that are separated, in time, by less than one millisecond or less than 0.5 millisecond. This is because DLS may measure 'rapidly-fluctuate physical phenomena' which fluctuate on a sub-millisecond time scale. Conventional PPG devices operate (for example, to derive concentration parameters) by quantifying data trends over a time scale of around 10 milliseconds.

In one example, autocorrelation techniques are used. In another example, power spectrum techniques are used. In yet another example, it is possible to compute standard deviations of the 'frequent measurements' where consecutive measurements have time gaps of less than 0.5 milliseconds. These statistical functions (or any other statistical function) may be computed for at least 100 measurements that occur within a period of time that is at most 40 milliseconds or for at least 250 measurements that occur within a period of time that is at most 100 milliseconds or for at least 500 measurements that take place within a time period that is at most 200 milliseconds.

As shown in FIG. 3, there are two types of dynamic light scattering measurements. The example on the left hand side of FIG. 3 relates to 'single scattering' whereby photons emitted by the coherent light source 104 collide only once (and are hence redirected) with one of the scatterers (typically a RBC or an aggregate thereof) before being re-directed by the scatterer and reaching photodetector 108. In the example on the right hand side of FIG. 3, the photons are subjected to multiple collisions with scatterers before reaching the photodetector. In the example of FIG. 3, for the 'single scattering case' the offset distance d1 between light source 104 photodetector 108 is relatively small—for example, less than 4 mm or less than 3 mm or less than 2.5 mm. For the 'multiple scattering case' the offset distance d2 between light source 104 photodetector 108 may be larger—for example, at least 6 mm or around 10 mm.

The aforementioned examples where DLS is used to detect pulse rate, plasma viscosity or RBC aggregate size may relate primarily to the 'single scatter' case where a DLS measurement based primarily on single-scatter events is carried out. In addition, WO 2008/053474 discussed a 'multiple scatter' application (with reference to FIG. 18 of WO 2008/053474 and to the accompanying discussion on page 20) where a DLS measurement of oxygen saturation based primarily on multiple-scatter events is carried out. This specific example relates to 'multi-wavelength' DLS.

The following patent documents and non-patent publications describe potentially relevant background art, and are each incorporated herein by reference in their entirety: WO 2008/053474, U.S. Pat. No. 4,928,692, U.S. Pat. No. 4,960,126, U.S. Pat. No. 6,793,256, U.S. Pat. No. 6,763,256; U.S. Pat. No. 5,598,841, U.S. Pat. No. 6,553,242, U.S. Pat. No. 7,336,982 and U.S. Pat. No. 7,018,338.

SUMMARY OF EMBODIMENTS

Embodiments of the present invention relate to a method and apparatus whereby a 'light-absorption related blood analyte concentration parameter(s)' may be determined according to a temporal correlation between photoplethysmography data (e.g. pulse oximeter data) and DLS data. One salient feature of the DLS data is that it provides a 'rheological measurement' of the flow conditions that prevail within the subject's peripheral blood vessels. As will be discussed below, the aforementioned one 'rheological pulse measurement' may provide a description of the timing and/or wave form of the pulse-induced pressure wave within the peripheral blood vessels that is both accurate as well as robust (e.g. much more robust than PPG measurements) to 'noise' such as motion artifacts and the presence of (or motion of) venous blood a the PPG measurement site.

Not wishing to be bound by any particular theory, the present inventors have observed that (i) DLS is a useful tool for measuring temporal or spatial changes in shear stress due to blood flow changes within peripheral blood vessels which are typically small; (ii) the local shear stress measurement provides an accurate description of the pulse-induced pressure wave even in small blood vessels; and (iii) by effecting a DLS measurement and/or measurement of shear stress within the peripheral blood vessels it is possible to directly probe the pulse-induced pressure wave within the subject's peripheral blood vessels (for example, at or near the measurement location). A 'rheological measurement device' (e.g. DLS device) may 'directly measure' the pulse-induced pressure wave by reflection energy from and/or driving energy through at least a portion of a blood vessel (e.g. peripheral blood vessel) and analyzing patters in energy reflected by and/or deflected by and/or transmitted through the peripheral blood vessels.

Examples of light-absorption related blood analyte concentration parameter include but are not limited to blood oxihemoglobin saturation, blood oxihemoglobin absolute concentration and blood carboxyhemoglobin concentration or saturation.

According to a first embodiment, it may be useful to synchronize the photoplethysmography data 'around' the local-pulse descriptive additional data (for example, DLS data, local shear stress data, or any other local-pulse descriptive data acquired by locally probing the pressure pulse-induced pressure wave). This synchronization may be useful in order to associate each photoplethysmography measurement with a particular stage or phase of the pulse-induced local pressure wave (which may mimic the cardiac cycle and thus include systolic and diastolic stages and sub-stages thereof).

In one example, it is possible to determine from the DLS data which photoplethysmography measurements are acquired at a point in time 'near the peak' and which photoplethysmography measurements are acquired 'near the valley' associated with the local pressure wave within the patient's blood vessels. This measured local pulse timing information may be useful for properly interpreting the pulse photoplethysmography measurements in order to determine the relative contributions of the AC and DC components to the absorption signal measured by the photoplethysmography device. In this way, it is possible to use the DLS measurements as a 'temporal trigger' for interpreting the photoplethysmography measurements.

Using the 'additional local signal' obtained by locally probing the pulse-driven pressure wave may be particularly useful when the photoplethysmography data is relatively 'noisy' so that timing of photoplethysmography measurements relative to the pulse-induced local pressure wave at the measurement site is not always clear a priori. For example, this may occur under poor perfusion conditions and/or when the photoplethysmography (PPG) signal is a reflection photoplethysmography signal such as a reflection oximetry signal (rather than a transmission oximetry signal) and/or in situations where motion artifacts are significant.

According to a second embodiment, it may be possible to attach more significance (i.e. for the purpose of computing a light-absorption related blood analyte concentration parameter(s)) to photoplethysmography data acquired at times when there is a stronger correlation between photoplethysmography data and the additional data obtained by locally probing the pulse-driven pressure wave. Other data acquired at times when the correlation is weaker may be either discarded or assigned a lesser weight when computing a temporal-weighted average of input data to obtain the light-absorption related blood analyte concentration parameter.

In one example, this may be useful for de-emphasizing time periods where contribution of motion artifacts to the photoplethysmography measurement signal is more significant. In another example, this may be useful for correcting for the presence of venous blood (for example, venous blood whose dynamics is, at least in part, pulse or/and motion-driven).

For the particular case of DLS measurements (i.e. where the 'additional data obtained by locally probing the pulse-driven pressure wave' is DLS data), the present inventors have observed that under good perfusion conditions and when motion artifacts do not play a significant role the correlation between the DLS signal and the derivative of the plethysmography signal.

Although the present inventors believe that shear stress measurements provide a particularly useful tool for directly probing the pulse-induced pressure wave within a peripheral blood vessel, it is now disclosed that other techniques and tools may be used to directly probe the pulse-induced pressure wave within the peripheral circulatory system for the purpose of improving the accuracy of photoplethysmography measurements of light-absorption related blood analyte concentration Tools and/or techniques for carrying out this 'rheological measurement' of the pulse-driving pressure wave within the peripheral circulatory system include but are not limited to: (i) acoustic or optical Doppler measurements of flow velocity (for example, by measuring the velocities of suspended particles) or a flow velocity profile at or near the measurement location; (ii) measurements of skin impedance at or near the measurement location; (iii) measurements of light interference or of light frequency shifts (e.g. of coherent light) at or near the measurement location; and (vi) an acoustic or photoacoustic measurement (for example, ultrasound measurement) of the skin.

It is now disclosed a method of measuring one or more light-absorption related blood analyte concentration parameters of a mammalian subject, the method comprising:

a) effecting a photoplethysmography (PPG) measurement of the subject by illuminating skin of the subject with at least two distinct wavelengths of light and determining relative absorbance at each of the wavelengths;

b) effecting a dynamic light scattering measurement (DLS) of the subject to rheologically measure a pulse parameter of the subject;

c) temporally correlating the results of the PPG and DLS measurements; and d) in accordance with the temporal correlation between the PPG and DLS measurements, assessing value(s) of the one or more light-absorption related blood analyte concentration parameter(s).

In some embodiments, blood analyte concentration parameter is selected from the group consisting of a blood oxihemoglobin concentration parameter, a blood carboxyhemoglobin concentration parameter and an arteriovenous oxygen difference (AV difference) parameter.

In some embodiments, the temporal correlating and/or value assessing includes:

i) determining from the measurement of step (b) a description of a pulse timing; and ii) in accordance with the DLS pulse-timing determining, associating each PPG measurement of a plurality of measurements with a different respective pulse-relative time value describing a pulse-relative temporal position of the PPG measurement within the pulse; and iii) determining the light-absorption related blood analyte concentration parameter in accordance with pulse-relative temporal positions.

I In some embodiments, the pulse-relative temporal position describes at least one of:

i) a time elapsed between the occurrence of a pulse event and the subsequent measurement time of PPG data; and ii) a time elapsed between the measurement time of PPG data and an occurrence of a subsequent pulse event.

In some embodiments, the pulse event is selected from the group consisting of an initiation of the systolic phase, a peak of the systolic phase, an initiation of the diastolic phase, and a zero-crossing of a time derivative of a pulse value.

In some embodiments, the DLS is single scattering DLS and/or single wavelength DLS.

In some embodiments, the DLS measurement and the PPG measurements are local to each other.

In some embodiments, step (d) includes:

i) computing a parameter descriptive of the temporal correlation between measurements of step (b) and step (c); and ii) in accordance with the computed temporal correlation parameter, determining a time-dependent PPG data quality value associated with each PPG measurement; and iii) computing the light-absorption related blood analyte concentration parameter(s) by assigning greater weight to PPG data having a higher data quality value and lesser or no weight to PPG data having a higher data quality value.

It is now disclosed a method of measuring one or more light-absorption related blood analyte concentration parameters of a mammalian subject, the method comprising:

a) effecting a photoplethysmography (PPG) measurement of the subject by illuminating skin of the subject with at least two distinct wavelengths of light and determining relative absorbance at each of the wavelengths;

b) effecting a non-PPG rheological pulse measurement to rheologically measure a pulse parameter of the subject;

c) temporally correlating the results of the PPG and rheological measurements; and d) in accordance with the temporal correlation between the PPG and rheological pulse measurements, assessing value(s) of the one or more light-absorption related blood analyte concentration parameter(s).

In some embodiments, the effecting of the non-PPG rheological pulse measurement includes effecting at least one of:

a) a speckle analysis;

b) a measurement of a blood shear stress;

c) a light interference measurement;

d) a acoustic or optical Doppler measurement; and e) an electrical impedance measurement.

In some embodiments, the blood analyte concentration parameter is selected from the group consisting of a blood oxihemoglobin concentration parameter, a blood carboxyhemoglobin concentration parameter and an arteriovenous oxygen difference (AV difference) parameter.

It is now disclosed a method of measuring blood parameters of a mammalian subject, the method comprising:

a) effecting a photoplethysmography (PPG) measurement of the subject by illuminating skin of the subject with at least two distinct wavelengths of light and determining relative absorbance at each of the wavelengths;

b) effecting a dynamic light scattering measurement (DLS) of the subject to rheologically measure a pulse parameter of the subject;

c) temporally correlating the results of the PPG and DLS measurements; and d) in accordance with the temporal correlation between the PPG and DLS measurements, assessing a venal contribution and/or relative contributions of arterial and venal blood to one or more light-absorption related blood analyte concentration parameter(s).

It is now disclosed a method of measuring one or more light-absorption related blood analyte concentration parameters of a mammalian subject, the method comprising:

a) effecting a photoplethysmography (PPG) measurement of the subject by illuminating skin of the subject with at least two distinct wavelengths of q light and determining relative absorbance at each of the wavelengths;

b) effecting a non-PPG rheological pulse measurement to rheologically measure a pulse parameter of the subject;

c) temporally correlating the results of the PPG and rheological measurements; and d) in accordance with the temporal correlation between the PPG and rheological pulse measurements, assessing a venal blood contribution and/or relative contributions of arterial and venal blood to one or more light-absorption related blood analyte concentration parameter(s) and/or relative volumes or flow rates of arterial and venal blood.

It is now disclosed a method for measuring one or more light-absorption related blood analyte concentration parameters of a mammalian subject, the system comprising:

a) a photoplethysmography (PPG) device configured to effect a PPG measurement by illuminating skin of the subject with at least two distinct wavelengths of light and determining relative absorbance at each of the wavelengths;

b) a dynamic light scattering measurement (DLS) device configured to effect a DLS measurement of the subject to rheologically measure a pulse parameter of the subject; and c) electronic circuitry configured to:

i) temporally correlate the results of the PPG and DLS measurements; and ii) in accordance with the temporal correlation between the PPG and DLS measurements, assess value(s) of the one or more light-absorption related blood analyte concentration parameter(s).

It is now disclosed a system for measuring one or more light-absorption related blood analyte concentration parameters of a mammalian subject, the system comprising:
a) a photoplethysmography (PPG) device configured to effect a PPG measurement by illuminating skin of the subject with at least two distinct wavelengths of light and determining relative absorbance at each of the wavelengths;
b) a dynamic light scattering measurement (DLS) device configured to effect a DLS measurement of the subject to rheologically measure a pulse parameter of the subject; and
c) electronic circuitry configured to:
  i) temporally correlate the results of the PPG and DLS measurements; and
  ii) in accordance with the temporal correlation between the PPG and DLS measurements, assess a venal blood contribution and/or relative contributions of arterial and venal blood to one or more light-absorption related blood analyte concentration parameter(s) and/or relative volumes or flow rates of arterial and venal blood.

BRIEF DESCRIPTION OF THE DRAWINGS

FIG. 9 illustrates certain optical component geometries according to some embodiments.

FIGS. 10A-10B illustrate a wrist-deployed derive for measuring a blood oxygen saturation parameter.

FIGS. 11A-11C and FIG. 5 relate to a certain use scenario where it is possible to obtain a corrected blood oxygen saturation parameter that is corrected for the presence of venous blood.

FIGS. 12A-12E relate to a experimental scenario where it is possible to obtain a corrected blood oxygen saturation parameter that is corrected to deemphasize motion artifacts.

FIGS. 13-14, 15A, 15B, 15C, 15D, 15E and 15F relate to DLS apparatus, routines, and experiments for locally measuring a pulse-induced local pressure wave within a peripheral blood vessel.

FIG. 16A-16B respectively illustrate a flow chart of a routine and a block diagram of an apparatus for measuring a blood oxygen saturation parameter according to a PPG measurement and an additional local measurement of a pulse-induced local pressure wave within the peripheral blood vessel in accordance with some embodiments.

DETAILED DESCRIPTION OF EMBODIMENTS

Figure 1:
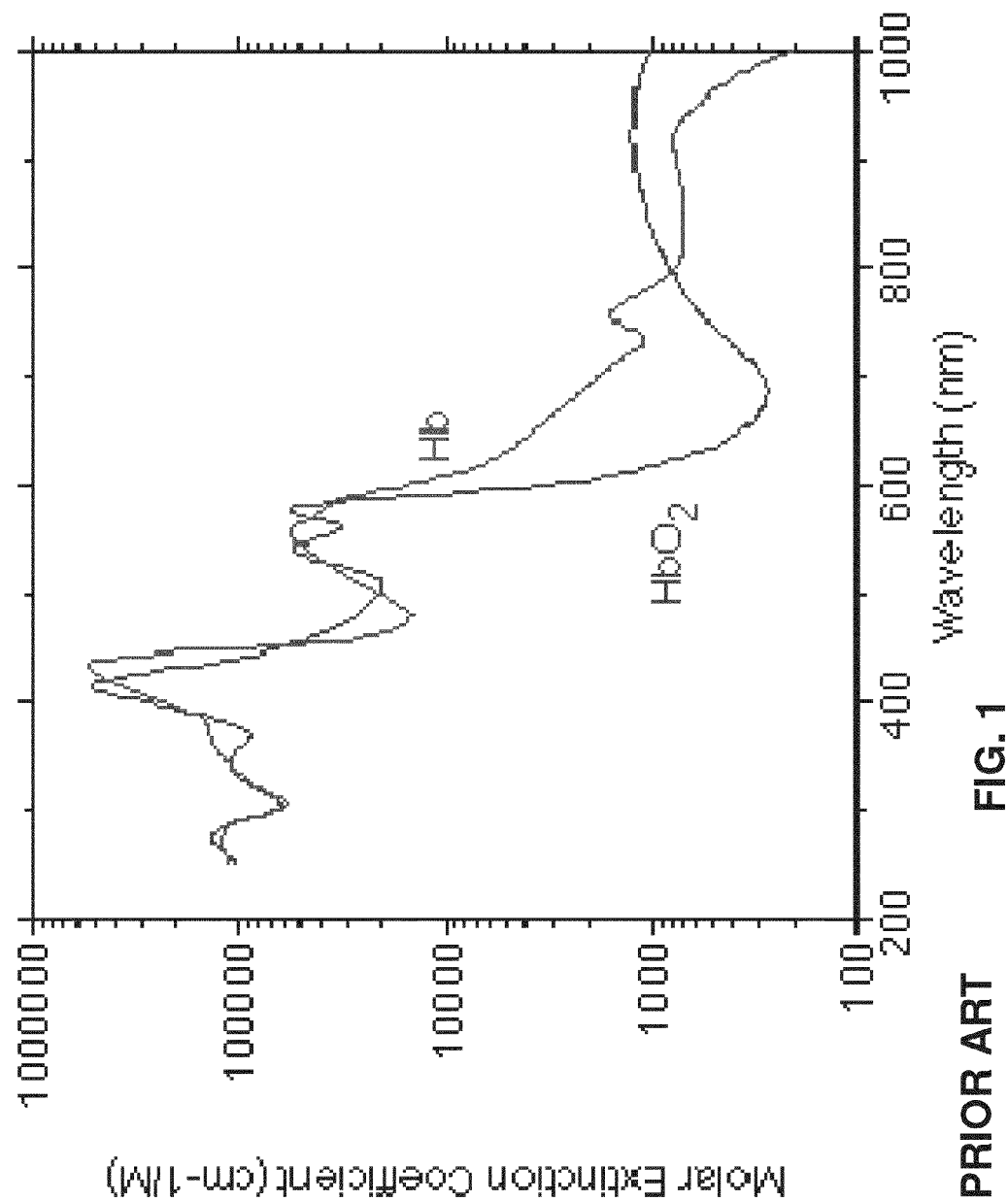
FIG. 1 illustrates extinction curves for both hemoglobin and oxihemoglobin (prior art).
Figure 2:
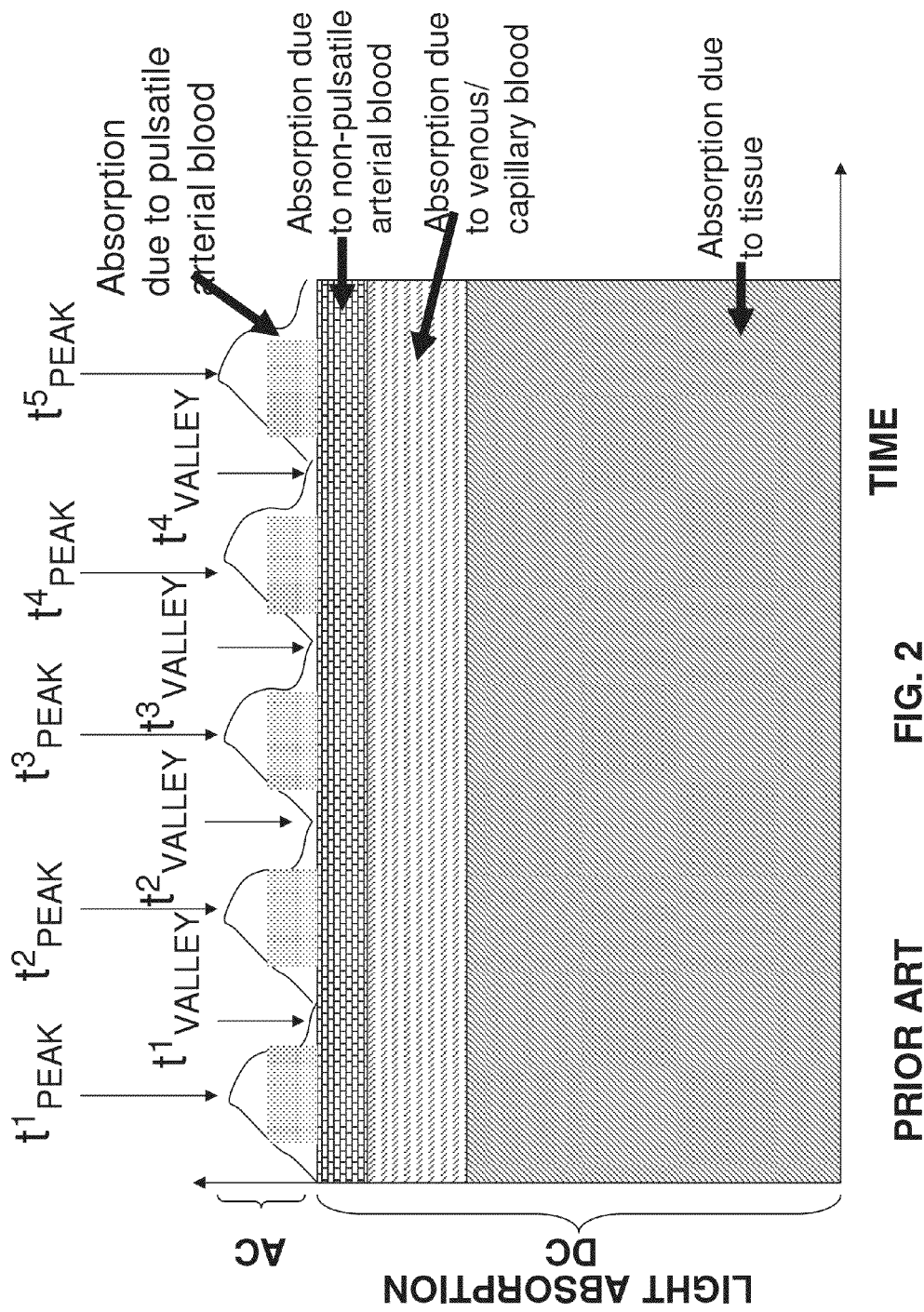
FIG. 2 illustrates the time-dependent light absorption curve as measured by oximeters and the time dependency of various components contributing to light absorption (prior art).
Figure 3:
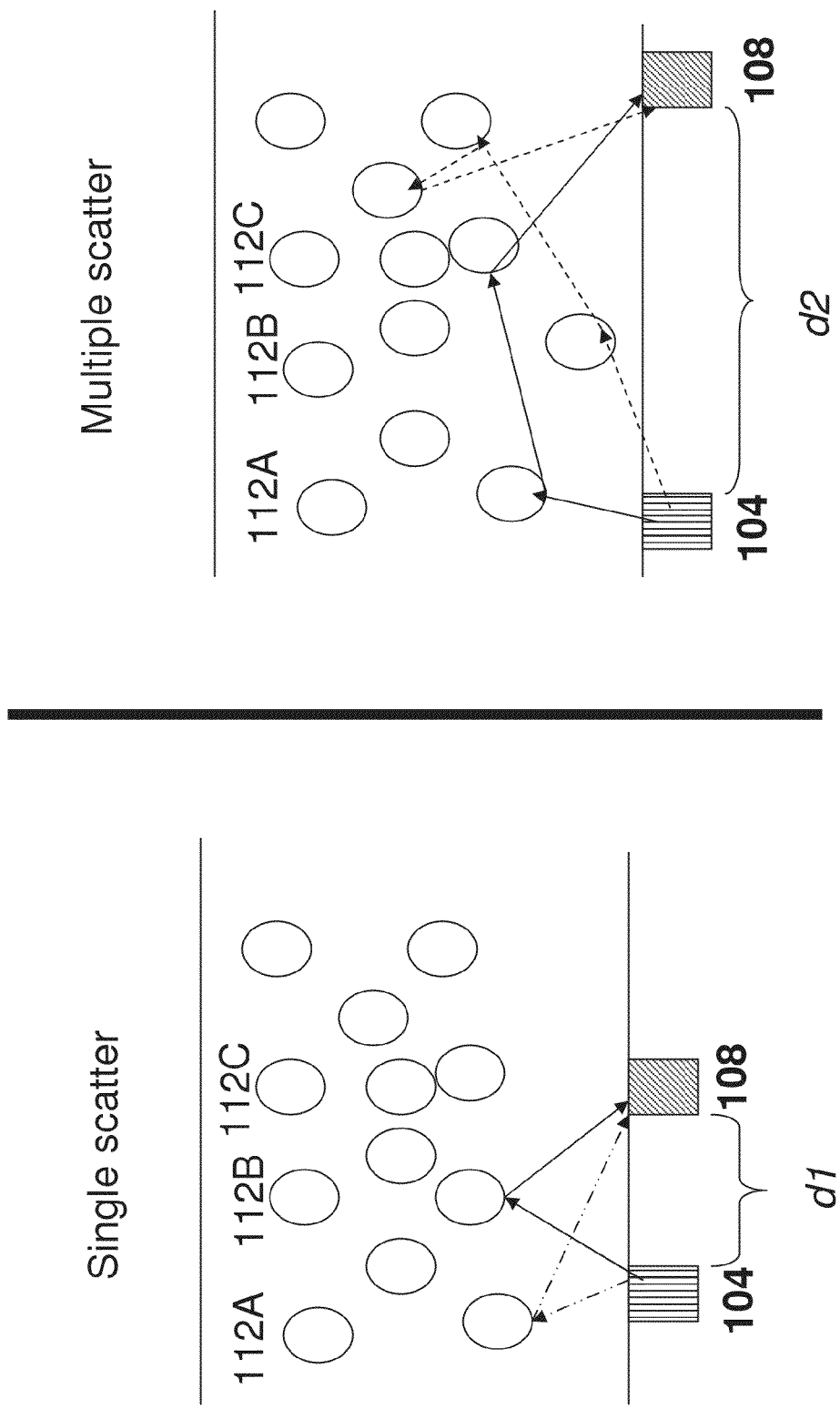
FIG. 3 illustrates the difference between single-scatter DLS and multiple-scatter DLS.

The claims below will be better understood by referring to the present detailed description of example embodiments with reference to the figures. The description, embodiments and figures are not to be taken as limiting the scope of the claims. It should be understood that not every feature of the presently disclosed methods and apparatuses is necessary in every implementation. It should also be understood that throughout this disclosure, where a process or method is shown or described, the steps of the method may be performed in any order or simultaneously, unless it is clear from the context that one step depends on another being performed first. As used throughout this application, the word "may" is used in a permissive sense (i.e., meaning "having the potential to'), rather than the mandatory sense (i.e. meaning "must").

A number of features are described in the present disclosure. The skilled artisan will appreciate that any embodiment will provide any combination of features described herein.

Embodiments of the present invention relate to the observations that (i) both optical plethysmography (PPG) signals (e.g. an oximeter signal) and the DLS signal obtained by speckle analysis are temporally correlated to the pulse-driven pressure wave within the subject's peripheral blood vessels under 'ideal conditions' (for example, 'good perfusion' conditions and/or when the oximeter data is from a transmission oximeter and/or when the role of motion artifacts is marginal); (ii) in less ideal situations the strength of the temporal correlation between the DLS signal and the pulse-driven pressure wave in peripheral blood vessels exceeds (maybe even greatly exceeds) the strength of the temporal correlation between the PPG signal and the pulse-driven pressure wave in peripheral blood vessels.

Notwithstanding the fact that both DLS measurements and PPG measurements are both derived from optical responses of the subject's blood at substantially a single measurement location, the strength of the temporal correlation of the DLS signal to the timing of the pressure wave in peripheral blood vessels may be much more 'robust' than that of the PPG signal. As such, it may be possible to rely on the fact that even under poor perfusion conditions and/or in the presence of motion artifacts, the DLS measurement still provide a reasonably accurate description of the timing of the local pulse-driven pressure wave at the PPG-signal measurement site.

This peripheral-blood-vessel pulse timing data (i.e. which is derived from DLS measurements and/or direct measurements of the sheer stress) can be correlated with the PPG signal in order to associate each PPG measurement with a respective elapsed time since a most recent pulse event (e.g. initiation of the systolic phase, peak of the systolic phase, initiation of the diastolic phase or any other pulse event). In one example, it is possible to more accurately determine relative magnitudes of the AC and DC contributions to the PPG signal if it is known that a first PPG measurement occurs at a time that is substantially a wave 'peak' time and if a second PPG measurement occurs at a time that is substantially a wave 'valley' or 'trough' time—in this case, the difference between the first and second PPG measurements may describe the AC contribution to the PPG signal.

The aforementioned technique for determining the relative magnitudes of the AC and DC contributions according to peaks and valleys described in the previous paragraph is not intended as limiting. It will be appreciated that other routines for determining the relative magnitudes of the AC and DC contributions to the PPG signal may employ timing information of the DLS measurement and/or measurement of the oscillatory shear stress and/or any other local measurement of the timing of the pulse-induced local pressure wave in peripheral blood vessels.

As noted above, the present inventors have observed that shear stress measurements and/or flow profile measurements may be very useful for determining timing of the pulse-driven pressure wave in peripheral blood vessels.

DLS devices are a useful tool for directly measuring a location-dependent shear stress field within a peripheral blood vessel (i.e. a blood vessel which may be 'small'). In living subjects, pulse-induced pressure waves propagate within the subject's circulatory system. At each location within the subject's circulatory system, the wave form and/or phase of the pressure wave may differ. The present inventors believe that by 'directly' measuring the shear stress field changes (i.e. which describes the flow field) in peripheral blood vessels, it is possible to obtain a relatively accurate and robust description of the wave form and/or timing of the pressure wave in peripheral blood vessels. As noted above, it is possible to temporally correlate this wave form and/or timing information with PPG measurement data to obtain a more accurate measurement of an oxygen saturation parameter even under relatively 'poor' perfusion conditions.

Figure 4:
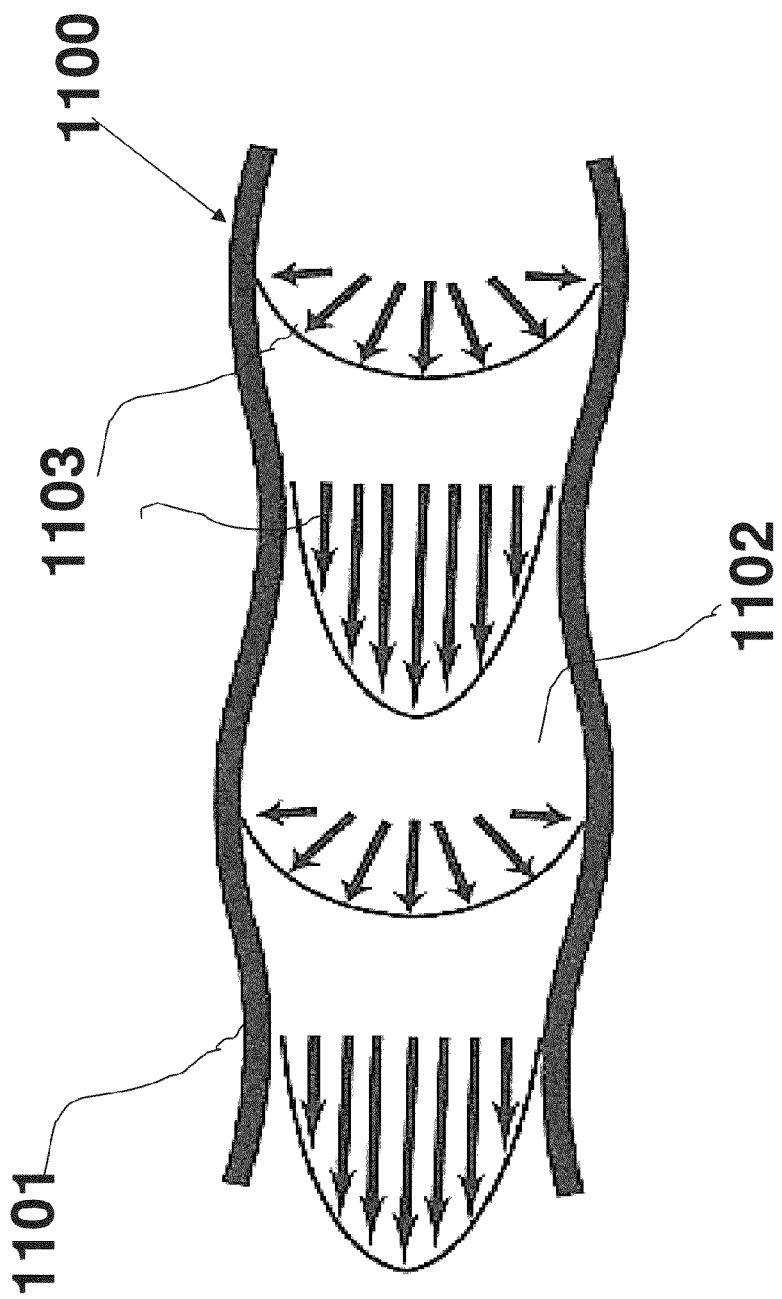
FIG. 4 illustrates shear flow (e.g. oscillatory shear flow) within a peripheral blood vessel.

Reference is now made to FIG. 4, illustrating pressure wave propagation in elastic vessel 1100 filled by the fluid 1101. Pressure changes cause local movements of the fluid 1101 and vessel wall 1102 in the form of a wave, so local velocity gradient (shear rate) 1103 oscillate. A more in-depth discussion describing the relationship between measured shear stress, DLS measurement and the pulse-timing features of the pulse-induced pressure wave in peripheral blood vessels is provided below with reference to FIGS. 13-15.

Embodiments of the present invention relate to the case where the 'second measurement' (i.e. other than the PPG measurement—for example, the rheological pulse measurement) is a direct measurement of a peripheral blood vessel. This is one preferred embodiment and not a limitation. In some embodiments, one or more of the PPG or the 'other' measurement (e.g. DLS) may be a direct measurement of another 'extra-cardial' (i.e. outside of the heart) location. For example, it may be possible to effect a PPG and/or DLS measurement even of the patient's neck (or any other 'poor perfusion location') to probe blood vessels other than peripheral blood vessel.

DEFINITIONS

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

The term 'concentration parameter' relates both to absolute concentrations as well as relative concentrations (for example, a saturation parameter; for example, a concentration relative to overall hemoglobin concentration or relative a concentration of another hemoglobin complex). A light-absorption related blood analyte concentration parameter relates to a concentration of a blood analyte having a distinctive absorption spectrum whose absolute or relative concentration is derivable from light absorption measurements. Examples of such blood analytes include oxihemoglobin and carbohyhemoglobin. In contrast, glucose is not a "light-absorption related blood analyte" because blood-residing glucose lacks the distinctive absorption spectrum.

The "light-absorption related blood analyte concentration parameter" may relate to the type of analyte (for example, oxihemoglobin or carbohyhemoglobin) as well as the type of blood (i.e. pulsatile or non-pulsatile blood, venous blood or arterial blood). A sum or difference or other function of a light-absorption related blood analyte concentration parameter may be considered a 'composite light-absorption related blood analyte concentration parameter.' One example of a 'composite light-absorption related blood analyte concentration parameter' is "arteriovenous oxygen difference" (AV difference) which reflects a difference between the oxygen content of arterial blood and mixed venous blood, and may be an important parameter, for example, in the field of anesthesiology.

In one example, the light-absorption related blood analyte concentration parameter(s)) is the concentration of $HbO2$ or is $SPO2$ which equals $HbO2/(Hb+HbO2)$. In another example, the light-absorption related blood analyte concentration parameter(s)) is the concentration of carboxyhemoglobin (HbCO) or the carboxyhemoglobin saturation (i.e. the ratio HbCO/(Total Hb) or MethHb/(Total Hemoglobin)).

In other embodiments, the light-absorption related blood analyte concentration parameter(s)) may relate to a concentration or saturation of any other derivative of Hemoglobin with a distinct spectrum feature It is appreciated that while the specific application of blood oxygen may relate to specific wavelengths described herein, the skilled artisan will be able to employ additional wavelengths (i.e. depending on the specific characteristics of the absorption spectrum) when measuring concentration-related parameters of other blood analyte (for example, other hemoglobin complexes).

The term 'direct measurement' (as opposed to 'indirect measurement') does not relate to whether or not a measurement entails an invasive procedure (for example, obtaining a blood sample). Instead, the term 'direct measurement' relates to a measurement primarily based on analyzing some sort of energy (for example, electromagnetic radiation such as light or other EM radiation, acoustic energy such as ultrasound, electrical currents for electrical impedance) which traverses and/or is deflected by and/or is reflected by a peripheral blood vessel or blood within the peripheral blood vessel. For the example of DLS devices, the energy is at least partially coherent light. The 'rheological measurement' of pulse is a 'direct measurement' of the pulse-induced pressure wave that is carried out by reflecting energy from and/or driving energy through at least a portion of a blood vessel such as an 'extra-cardial blood vessel' outside of the heart (for example, a peripheral blood vessel) and analyzing patters in energy reflected by and/or deflected by and/or transmitted through the peripheral blood vessels to probe flow patterns within the peripheral blood vessels. Parameters that may be measured in 'rheological measurement' include sheer stress, a flow profile, and suspended-particle velocity.

Optionally, and in some embodiments preferably, the 'rheological measurement' and/or DLS measurement may be a 'local measurement' substantially at (or near) the 'PPG measurement site.' For example, there may be a stronger correlation between the pulse signal at the PPG measurement site with other 'local' locations (and/or locations that are 'substantially the same').

A 'PPG measurement site' is the location where light is reflected and/or transmitted and/or deflected by biological tissue and/or blood. A location that is 'local' to the PPG measurement site (or 'substantially at the same location') is a location that is close to the measurement site—for example, less than 50 cm from or less than 40 cm from or less than 30 cm from or less than 20 cm or less than 10 cm or less than 5 cm or less than 3 cm or less than 2 cm or less than 1 cm from the measurement site). For this definition, it is appreciated that distance is measured along the surface of the skin rather than a Cartesian distance.

Figure 11A:
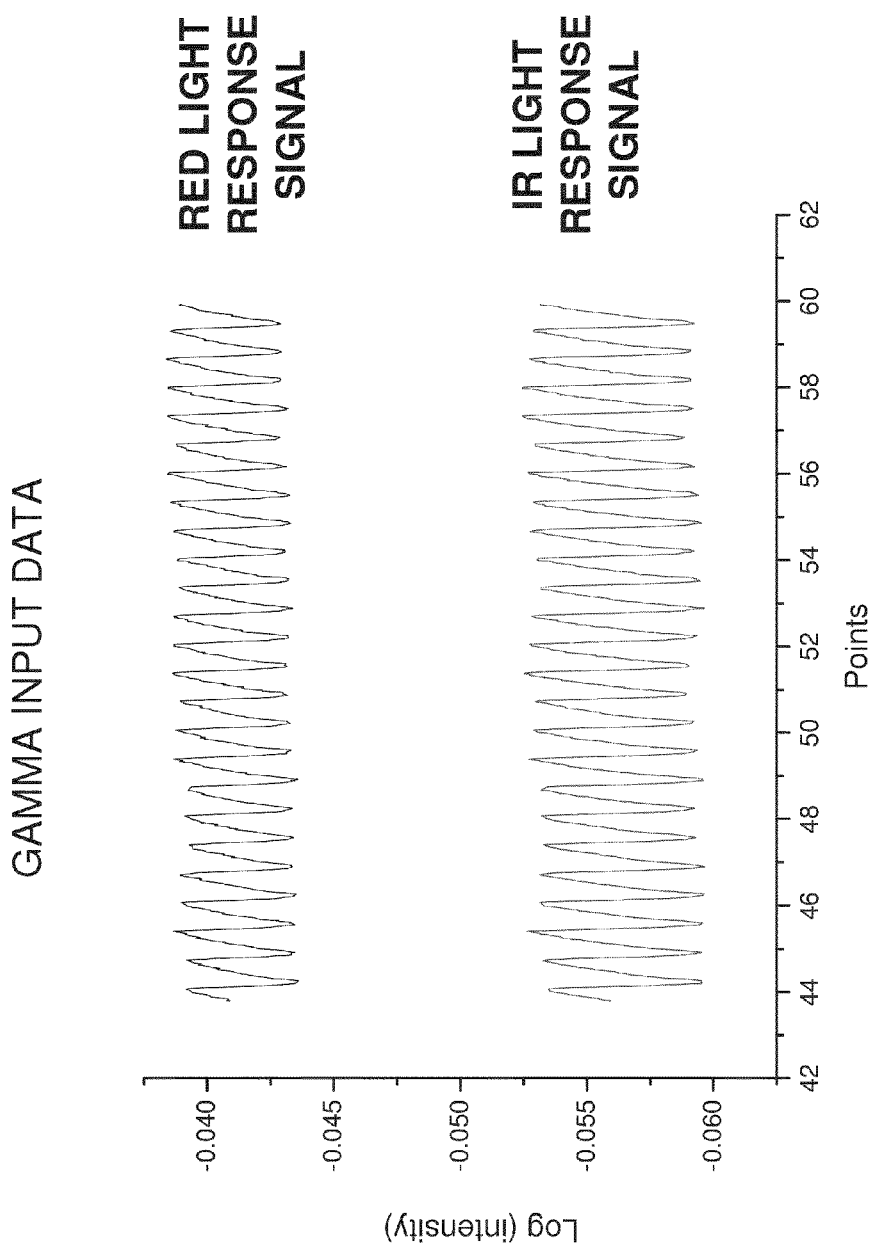
Figure 11B:
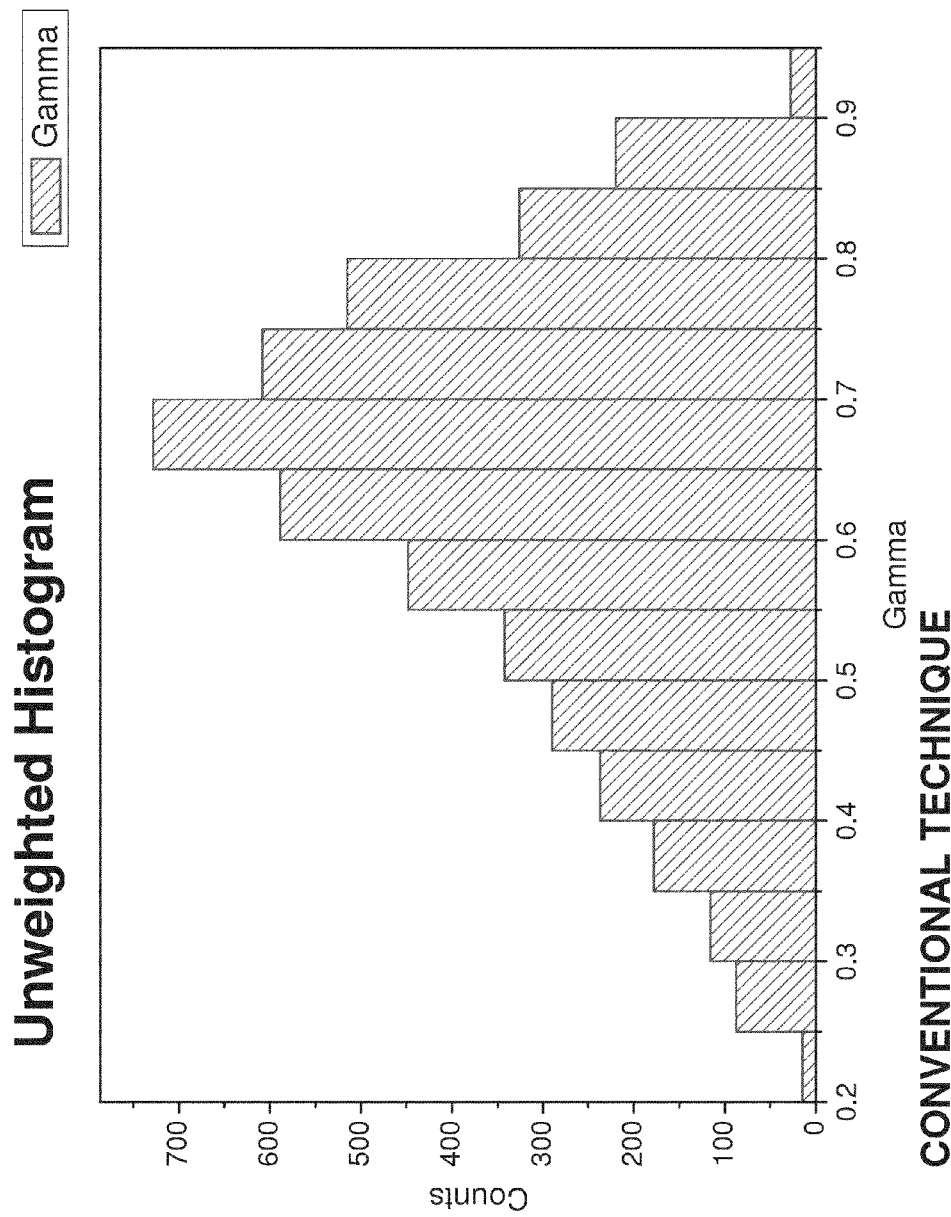
Figure 11C:
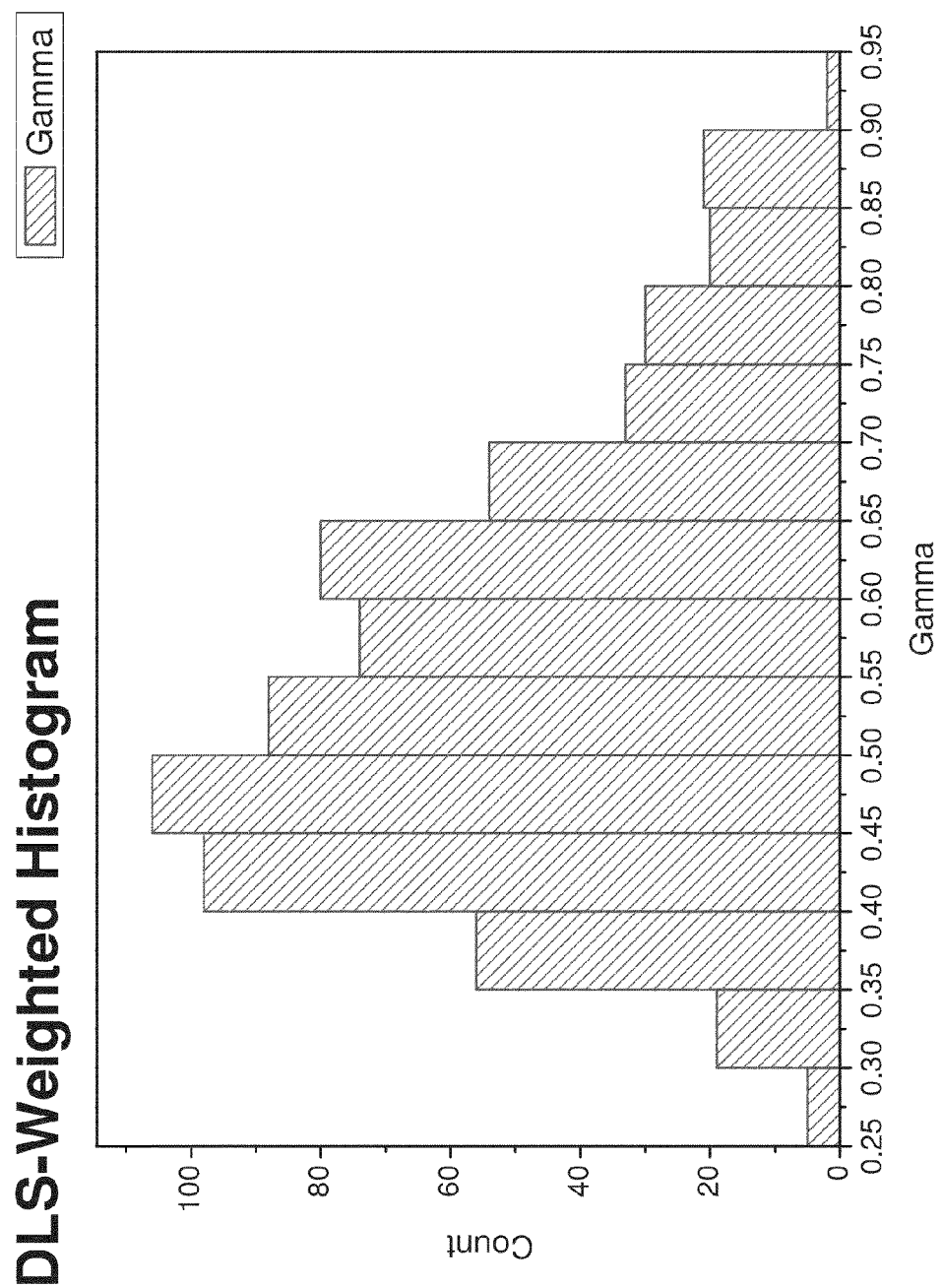
Figure 12A:
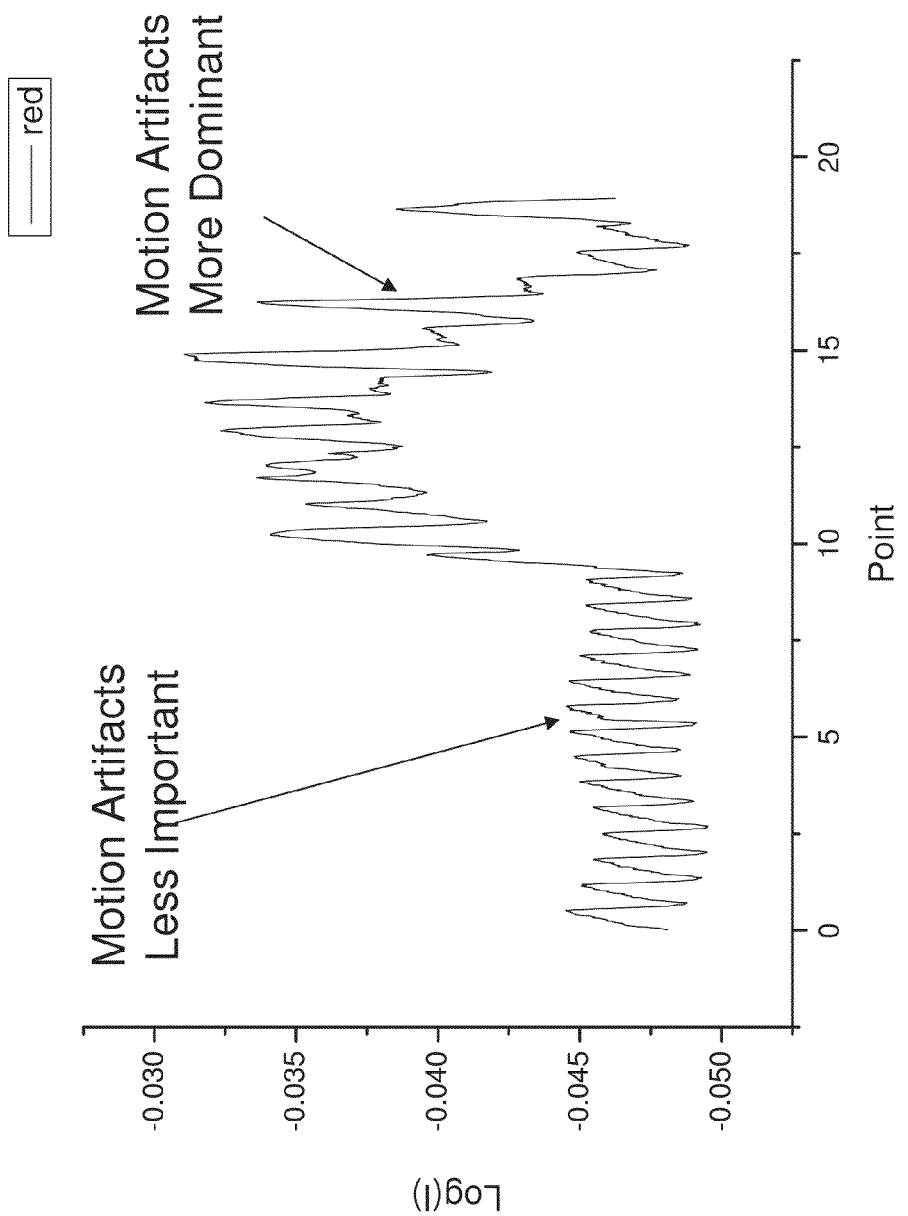

The present inventors have carried out a number of experiments illustrating the correlation between the PPG signal and the DLS signal (or another 'rheological pulse' signal) under various conditions. In a first experimental scenario (see FIG. 5; FIGS. 11A-11C relate to techniques for processing the data of FIG. 5), the subject was relatively motionless at a time when the PPG and the DLS measurement data were acquired. In a second experimental scenario (see FIG. 6, 12A-12B; FIGS. 12C-12E relate to techniques for processing the data of FIGS. 6, 12-12B), the subject was in motion part of the time while the PPG and DLS measurement data was acquired.

Figure 5:
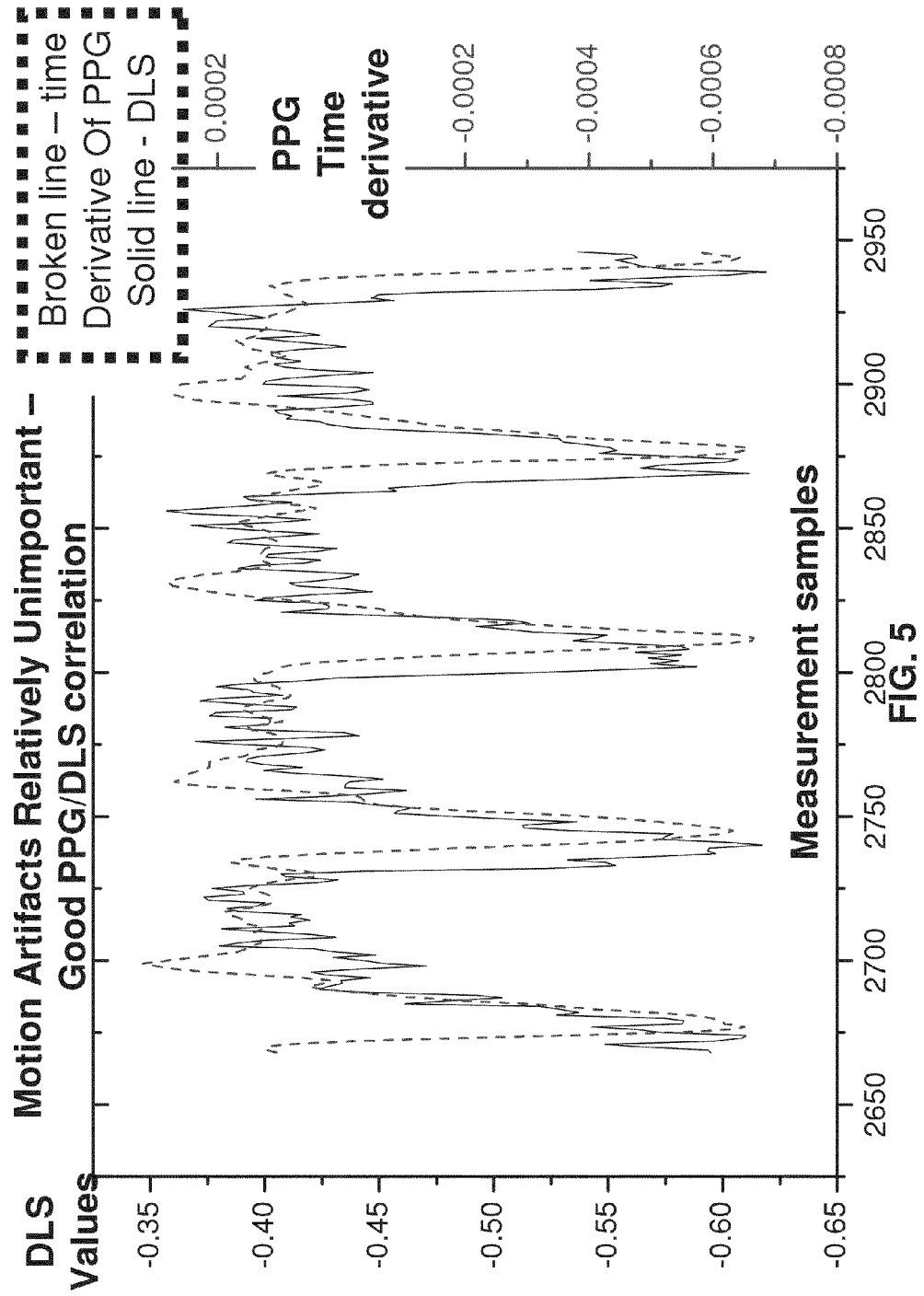
FIG. 5 illustrates experimental data describing the relatively strong (and relatively consistent) temporal correlation between PPG and DLS signals under conditions where motion artifacts (or other noise) are relatively unimportant.

FIG. 5 illustrates experimental data describing the relatively strong (and relatively consistent) temporal correlation between PPG and DLS signals under conditions where motion artifacts (or other noise) are relatively unimportant.

Figure 6:
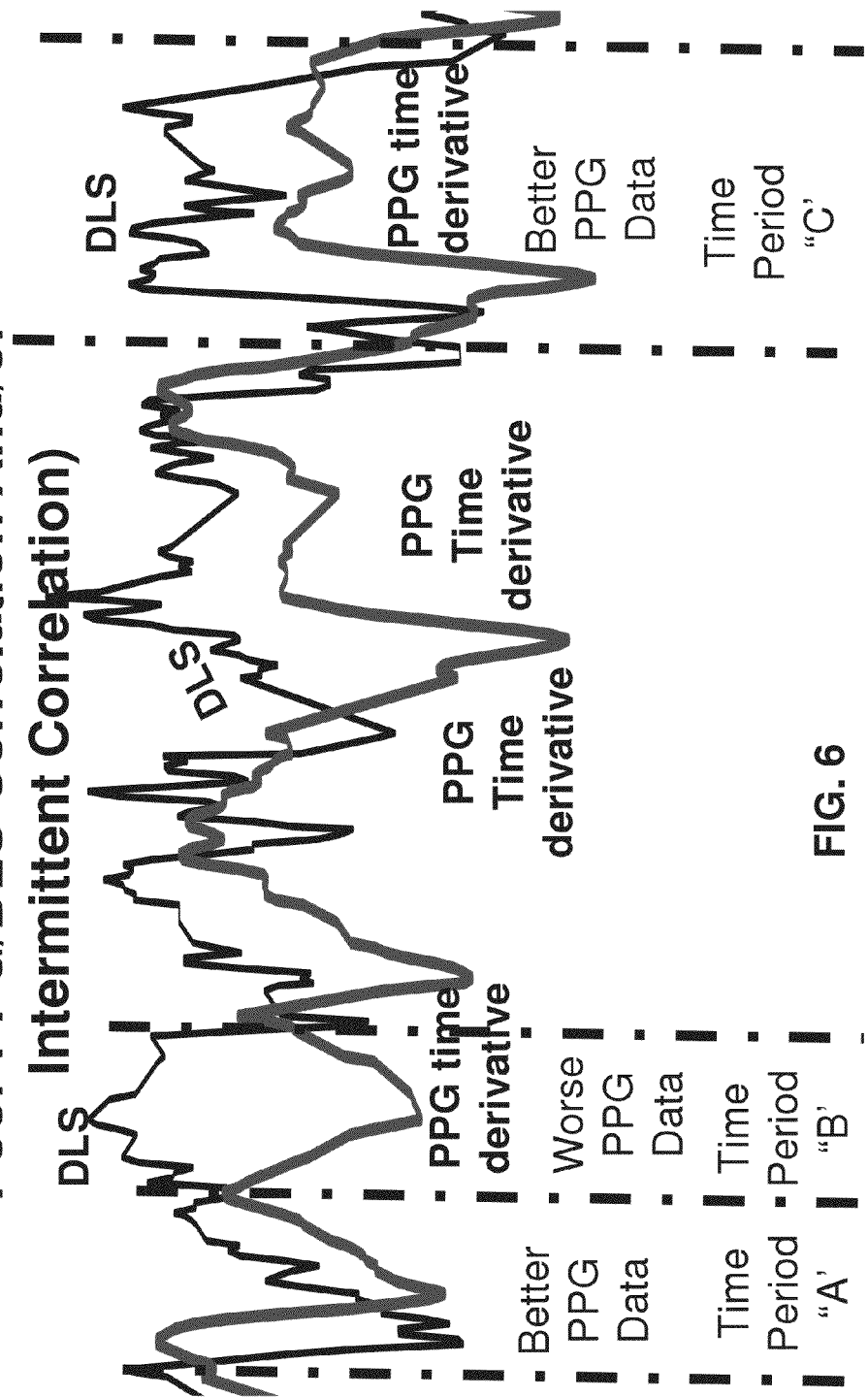
FIG. 6 illustrates experimental data describing the weaker and/or intermittent temporal correlation between PPG and DLS signals under conditions where motion artifacts (or other noise) are relatively unimportant.

FIG. 6 illustrates experimental data describing the weaker and/or intermittent temporal correlation between PPG and DLS signals under conditions where motion artifacts (or other noise) are relatively unimportant.

It may be observed from FIGS. 5-6 that the strength of the correlation of the DLS signal to the PPG signal is noticeably sensitive to motion artifact.

FIG. 7A is a flow chart of routine for deriving one or more light-absorption related blood analyte concentration parameter(s)) (for example, a blood oxygen saturation) according to some embodiments of the invention. In step S101, a PPG measurement is carried out at a measurement location. This may be carried out by any optical PPG device including but not limited to 'reflection' type PPG devices such as reflection oximeters (see, for example, FIG. 10 or any other reflection device) and transmission PPG devices (e.g. transmission oximeters). This may be carried out at any location on the patient including 'traditional PPG/oximeter locations' such as the ear lobe or finger tip as well as 'non-traditional' PPG/oximeter locations such as the write, forearm, upper arm, leg, chest or any other location.

In step S105, a DLS measurement and/or a measurement of the shear stress within a peripheral blood vessel and/or measurement of the local flow profile within the peripheral blood vessel is acquired at or near the measurement location. In step S109, light-absorption related blood analyte concentration parameter(s)) (for example, blood oxygen saturation) may be computed according to a function of the PPG and DLS measurement (for example, according to a temporal correlation between the PPG and DLS signals). One routine for effecting step S109 is described with reference to FIG. 8A; another routine for effecting step S109 is described with reference to FIG. 8B.

FIG. 7B is a block diagram of an apparatus 200 for measuring a light-absorption related blood analyte concentration parameter(s)) parameter in some embodiments. The apparatus 200 may include a PPG device 210, a DLS device 214, electronic circuitry 218 (for example, for processing the PPG and DLS data—for example, to effect the temporal correlation or to carry out any routine for computing a blood oxygen parameter described herein) and a display screen 222 (or any other data presentation or data transmission device including but not limited to an audio speaker and a wireless transmitter). It is appreciated that some components may be optionally shared between elements—for example, PPG and DLS device might share common electronic circuitry or may each respectively include their own electronic circuitry; furthermore, electronic circuitry 218 may be provided as a separately from both the PPG and DLS device, or may be including with the DLS or PPG circuitry).

In one non-limiting example, the PPG device can measure carbon carboxyhemoglobin concentration (e.g. either absolute concentration or a 'saturation value' relative to the total hemoglobin concentration). In this example, it might be advantageous to provide an audio alarm instead of or in addition to screen 222 to warn a user of dangerous blood carbon monoxide levels.

Figure 8:
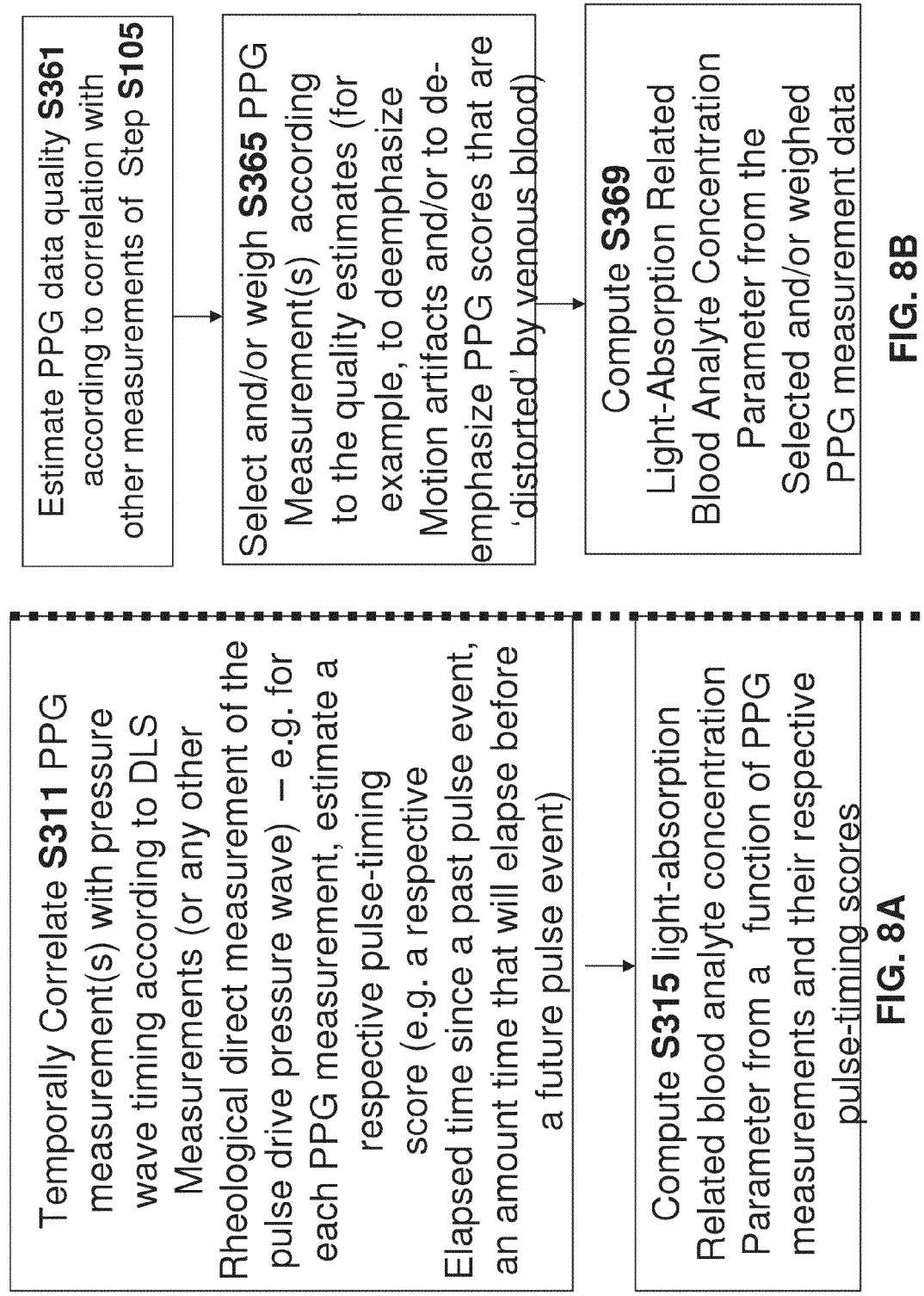
FIGS. 8A-8B illustrate certain routines for measuring a blood oxygen saturation parameter according to PPG and DLS measurement in accordance with some embodiments.

FIG. 8A-8B are flow charts of exemplary implementations of step S109. The skilled artisan will appreciate that these techniques may be combined with each other or other techniques.

In step S311 of FIG. 8A, the PPG measurements are temporally correlated with the DLS measurements to estimate a respective pulse-timing score—e.g. a respective elapsed time since a past pulse event within the peripheral circulatory stem or an amount time that will elapse before a future pulse event.

In one non-limiting example, the 'pulse event' may be the commencement of the 'pulse cycle'—for example, the commencement of the 'systolic stage' of the pulse. However, this is not a limitation, and it is possible to measure using DLS (or any other direct peripheral blood vessel pulse measurement device or any other rheological pulse measurement device) multiple pulse events and to temporally correlate the PPG signal with each of the pulse events to compute a concentration parameters (for example, according to respective timing scores such as elapsed time relative to all of the pulse event). In some embodiments, the frequency of the rheological and/or direct measurements of peripheral blood vessel pulse (i.e. which are used as multiple trigger times or synchronization times around which the PPG signal can be synchronized or temporally correlated for the purpose of computing a concentration parameter) may be one or more of (i) at least 2 or at least 5 or at least 10 or at least 50 rheological pulse measurements and/or pulse events within a single pulse cycle; and/or (ii) at least 2 or at least 5 or at least 10 or at least 50 pulse events 50 rheological pulse measurements and/or within a second. In some embodiments, these pulse events and/or rheological pulse measurements may be relatively 'evenly spaced' in time at a substantially constant frequency.

Exemplary pulse events include but are not limited to: (i) the commencement of the systolic or diastolic phase of the pulse, (ii) a slope event (i.e. where the first time derivative of the pulse signal changes sign or exceeds a number whose absolute value is at least 0.5 or at least 1 or at least 2 or at least 5 or at least 10 or any other number); (iii), a signal second derivative event (i.e. where the second time derivative of the pulse signal changes sign or exceeds a number whose absolute value is at least 0.5 or at least 1 or at least 2 or at least 5 or at least 10 or any other number); (iii) a 'linger time event' (i.e. where the value of the pulse signal or any time derivative thereof stays within a range (e.g. near zero or away from zero) for any measurable period of time); (iv) a 'spike event'—the occurrence of a brief spike (e.g. of duration less than 100 or less than 50 or less than 20 or less than 10 or less than 5 milliseconds) within the pulse signal or a time derivative thereof; and (v) a 'flat pulse event' where the pulse or a time derivative thereof stays substantially constant for any period of time that exceeds a time threshold (for example, at least 5 or at least 10 or at least 20 or at least 50 or at least 100 or at least 250 or at least 250 or at least 1000 milliseconds).

In one use case, the frequent rheological and/or direct measurement of peripheral blood vessel pulse (e.g. rheological pulse) an the frequency synchronizing around these frequent measurements may be useful for clinical situations where the magnitude of motion artifacts (or any other 'noise') fluctuates within a single pulse cycle. In one non-limiting example, the subject moves his hand 'half-way' into a pulse cycle—in this case, merely synchronizing around the 'commence pulse' event at the beginning of the systolic phase may cause erroneous PPG measurements of the concentration parameter because it relies only on 'outdated data.'

Reference is now made to FIG. 8B. In step S361, the PPG data quality may be estimated according to a correlation between PPG measurement data and DLS measurement (or any direct peripheral pulse measurement or rheological pulse measurement) data. For example, comparing FIGS. 5 and 6 demonstrates that the correlation is stronger during a relatively 'low noise situation,' and the correlation is weaker during a 'higher noise situation.' Thus, it is possible to determine, according to the strength of this correlation, the quality of the PPG data at any time. In the example of FIG. 6, it would be preferable to assign greater weight to PPG data acquired during time periods "A" or "C" and to discard (or assign less weight) to PPG data acquired during time period "B."

In FIG. 8B, as with FIG. 8A (or any other technique for utilizing rheological pulse data) it may be advantageous to carry out step S365 according to values of and/or trends in multiple DLS (or other direct or rheological pulse measurements) measurement values per pulse cycle. This frequency may be (i) at least 2 or at least 5 or at least 10 or at least 50 pulse events and/or rheological pulse measurements within a single pulse cycle; and/or (ii) at least 2 or at least 5 or at least 10 or at least 50 pulse events and/or rheological pulse measurements within a second. In some embodiments, these pulse events and/or rheological pulse measurements may be relatively 'evenly spaced' in time at a substantially constant frequency.

Thus, in step S365, 'good quality PPG measurements' and/or measurements from 'good PPG times' are selected and/or more heavily weighed. One example of step S365 for the case of an experiment performed by the present inventors is discussed below with reference to FIGS. 11B-11C and 12C-12E.

In step S369, the concentration parameter is computed according to the data weighting and/or selecting of step S365.

Not wishing to be bound by any particular theory, in some clinical situations, some types of 'noise' (i.e. noise for computing a pulsatile arterial concentration parameter for example oxygen saturation) may have a great detrimental effect on the accuracy of pulsatile arterial concentration parameter than other types of noise. For example, in clinical situation, magnitudes of errors introduced by the presence venous blood when measuring the pulsatile arterial concentration may be less than or much less than magnitudes of errors introduced by motion artifacts.

Not wishing to be bound by any particular theory, it is noted that in some embodiments, the usage of multiple 'rheological pulse' and/or 'direct pulse' measurements per pulse cycle (i.e. rather than synchronizing around a single one) may allow for a more accurate assessment of the pulse timing at different points in time throughout the pulse cycle to the point where it is possible to specifically measure the concentration of a light-absorption related venous blood analyte concentration parameter and/or a difference between (or quotient of or any other function of) a light-absorption related venous blood analyte concentration parameter and a corresponding overall blood and/or arterial blood concentration parameter value.

Figure 10A:
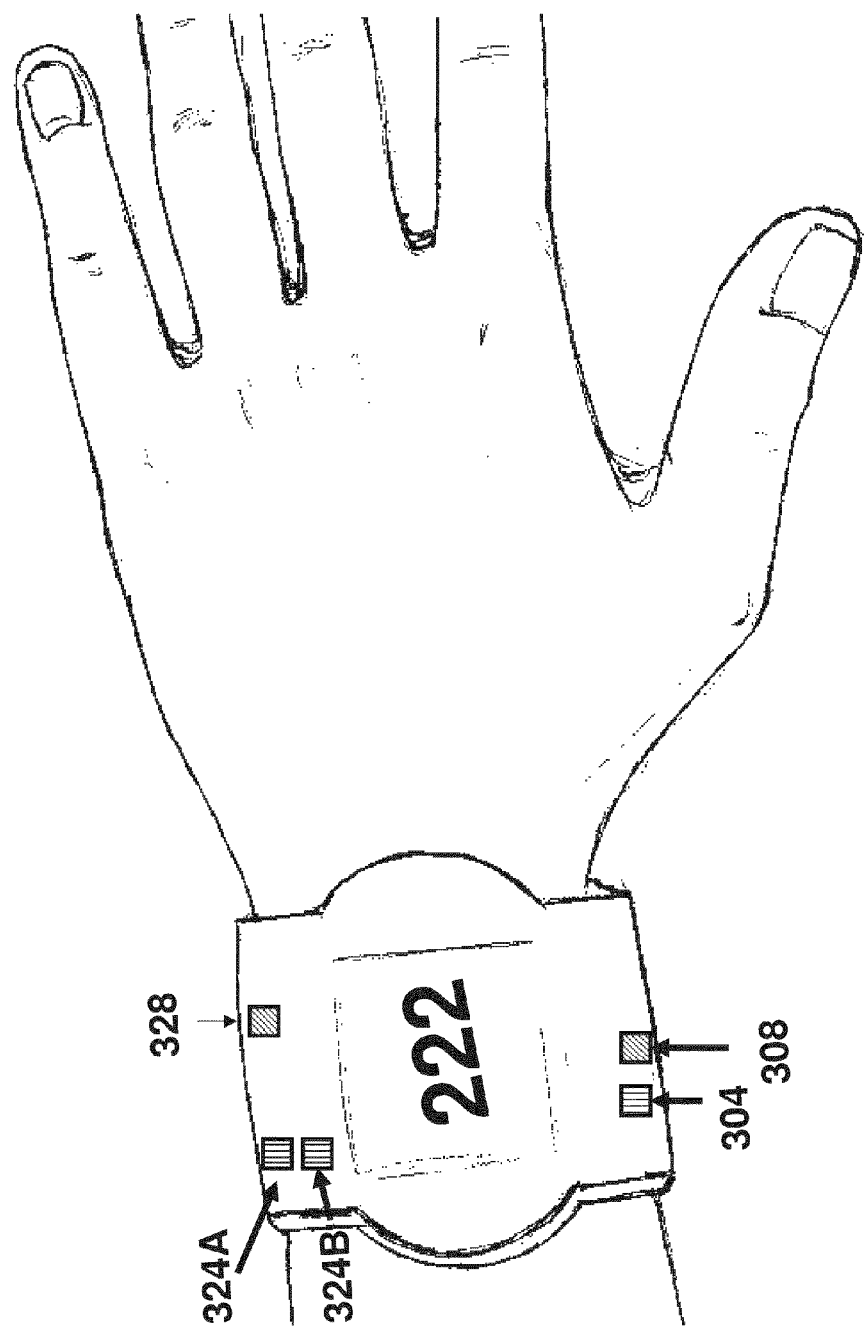

FIG. 9-10 illustrates non-limiting examples of certain geometries that may be used for optical components of the PPG and/or DLS apparatus. The term 'light source array' or 'detector array' refer to one or more light sources or one or more photodetectors. The PPG light source array may have at least two separate lights each light emitting light of a different respective wavelength. In another embodiments, the PPG light source array may have only a single light configured to emit multiple 'colors'—however, this might increase the cost of the device in non-limiting embodiments.

In non-limiting embodiments, the DLS measurement is 'single scatter DLS' and/or the distance $d_{DLS}$ between the locations of the DLS is relatively small. For example, $d_{DLS}$ may be less than 5 mm or less than 4 mm or less than 3 mm or less than 2 mm or less than 1 mm. In some embodiments, the ratio between $d_{PPG}$ and $d_{DLS}$ is at least 2 or at least 3 or at least 5 or at least 7 or at least 10.

In the example of FIGS. 9 and 10, the PPG and the DLS apparatus are 'local to each other' and acquirement measurement data from substantially the same location on the patient. This is not a limitation. In one non-limiting example, it may be possible to acquire PPG measurement data, for example, from the subject's left (right) hand and DLS (or any other rheological and/or direct pulse measurement data) from the subject's right (left) hand. Hand-foot techniques or apparatus (or other 'non-local' techniques or apparatus) are also possible.

There is no limitation on the wavelength of incoherent or coherent light that may be used. In some embodiments, the coherent light may include wavelengths between 350 nm and 1300 nm, for example, visible (for example, red) and/or near infra-red (NIR) light.

In one non-limiting example, the coherent light is red and/or NIR light which may be useful for determining a light of read and blood oxygen saturation and/or a blood hemoglobin concentration.

There is no limitation on the type of photodetector that may be used. For example, it may be possible to use a silicon detector for the range up to 1000 nm or InGaAS detector for tha range up to 1300 nm or CCD electronic camera as a photodetector.

In the example of FIG. 9, one or more of the optical components may be 're-used' both in the DLS and the PPG. In one example (see the bottom of FIG. 9) one or more of the light source (e.g. a coherent light source such as a laser) may function both for the PPG and the DLS measurements. For example, it may be possible to rely on the fact that the DLS probes relatively 'rapidly fluctuating phenomena' and generates measurement data according to 'rapid trends.' In contrast, the PPG probes 'slower fluctuating phenomena.' Thus, in some embodiments, it may be possible to electronically control a 'shared light' 330 to first function with PPG, then to function with DLS, and then to switch back. This may be useful to reduce the cost of manufacturing the device.

Example 1

Computing a Blood Oxygen Saturation Parameter in the Presence of Venous Blood

The present inventors have constructed a 'wrist hybrid PPG-DLS' device and have collected data from this device.

In FIG. 5 illustrates the results under relatively low motion artifacts' conditions. Although there is indeed a good correlation between the PPG and the DLS signal, it is nevertheless possible to employ the DLS device to remove the 'noise' of the venous blood. This technique may also be used to compute a arterial/venous blood concentration parameter relating the absolute and/or relative concentrations of arterial and venous blood.

FIGS. 11A-11C relate to the differentiation between venous and arterial components of the measured signal by using the DLS. One important calculated parameter in the pulse-oximetry is the so called Gamma (referred to as 'R' in the background section).

Gamma=(AC(red)/DC(red))/(AC(infrared)/DC(infrared).

Where AC is the pulsatile component of the signal and DC is the total intensity of the signal. "Red" corresponds to the signal being measured at wavelength of 670 nm and "infrared" corresponds to the signal being measured at 940 nm.

The calculated Gamma can be translated into the SPO2 (oxygen saturation) by using the universal calibration curve. According to this calibration, for example the Gamma ranging between 0.51-0.55 corresponds to SPO2 ranging between 99-96%, which is a normal value for the arterial blood. The venous blood saturation corresponds to the Gamma ranging about 0.8-0.9. Therefore, for the arterial blood reading of a healthy patient we expect to get Gamma 0.51-0.55.

In the following example of the wrist measurement it is shown that the measured Gamma was found about 0.65-0.68 which is beyond the normal range we expect for arterial blood.

FIG. 11A illustrates the PPG signal measured from the wrist during a certain measurement interval:

Based on this signal, at each few samples of the measurement the Gamma value is calculated. Afterword, by using a statistical averaging the average Gamma is calculated. The calculated Gamma is transformed into SPO2, according to the calibration curve.

FIG. 11B illustrated the distribution of Gammas being measured from the all pulses during 60 second of measurement. We can see that there the peak Gamma is about 0.65-0.7. This peak is chosen as Gamma representing the SPo2 of the patient during the measurement. Apparently Gamms=0.65-0.7 is an erroneous reading because it's far from the arterial blood Gamma (0.5-0.55).

Now we demonstrate that by using DLS signal we can decompose the histogram and to extract the right value of Gamma.

We take only the window points where the DLS signal is correlative with PPG signal near the crest points of the pulse. For these points the distribution illustrated FIG. 11C.

It is now evident that the peak of the distribution moved toward 0.5 which corresponds to real SPO2. This example demonstrated how the DLS signal help to reveal and to extract the measurement sessions which mostly represent the arterial blood.

Example 2

Computing a Blood Oxygen Saturation Parameter in the Presence of Motion Artifacts This example relates to an experiment where motion artifact where introduced (i.e. the subject moved his hand) after about 10 seconds. It is possible to see the strong change of the signal affects the PPG signal after 10 seconds (see FIG. 12A). The same signal may also be shown plotted together with DSL.

Figure 12B:
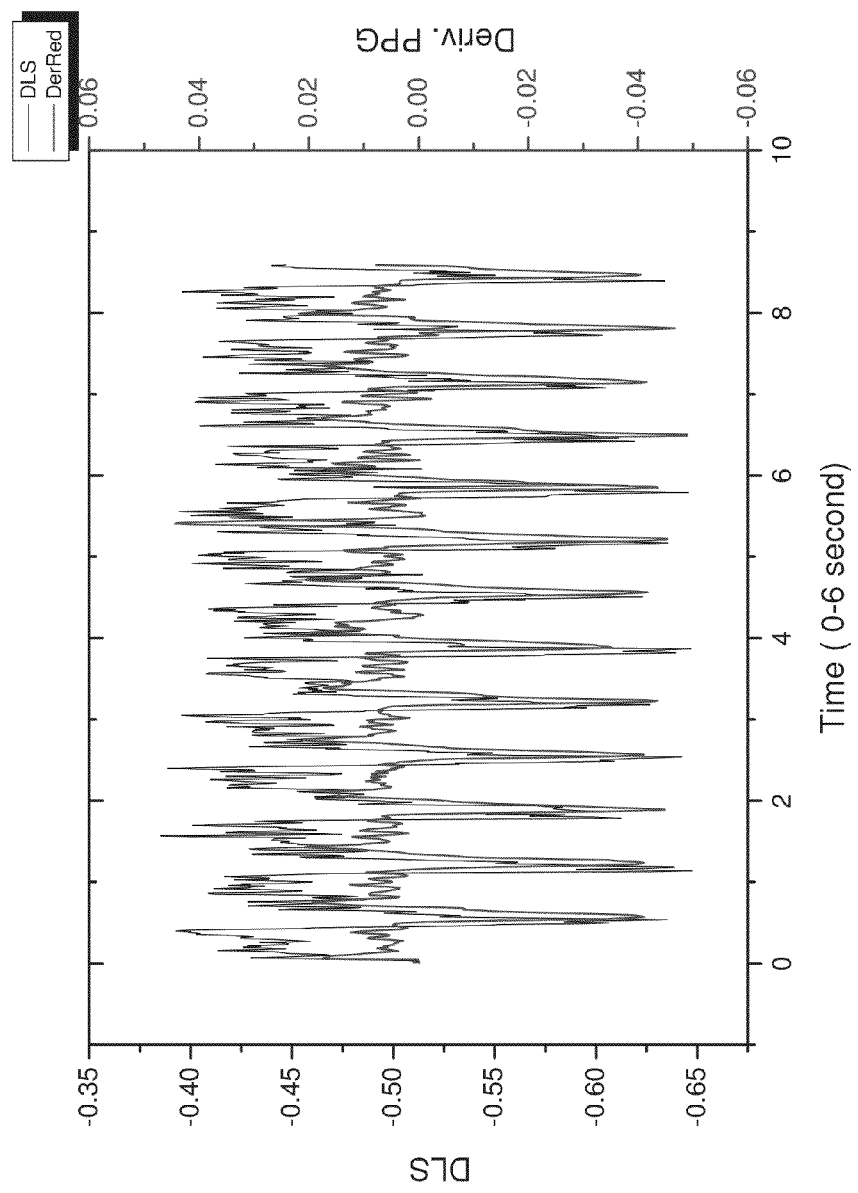
Figure 12C:
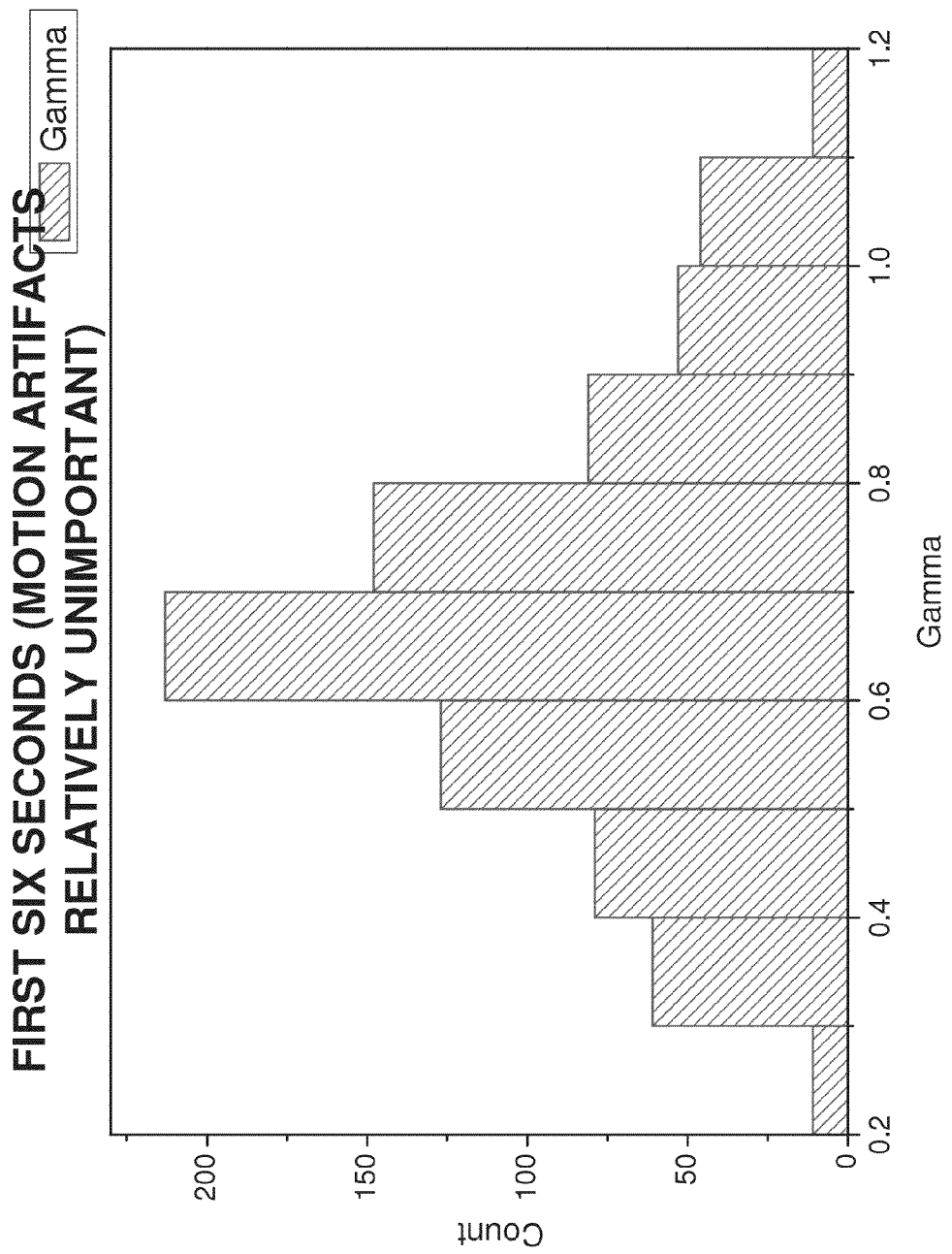

FIG. 12B shows this plot for the first 6 seconds (not many motion artifacts). FIG. 12C is the corresponding histogram plot for the case of the first 6 seconds FIGS. 12D-12E relate to the last 10 seconds during motion of the arm In FIG. 12E, certain PPG measurements are rejected (see, for example, step S365 of FIG. 8B)—the histogram is 'weighted'

After taking into consideration the DLS signal by rejected all uncorrelated with PPG values and by choosing an appropriated regions of PPG according to the predetermined limits of DLS value we get in the interval 10-20 second the gamma histogram of FIG. 12E.

It is evident from the figures that not only the motion artifacts but also venous blood artifacts have been rejected and the peak value around 0.55-0.6 is achieved A Discussion of a Relationship Between DLS and Local Pulse within the Peripheral Blood Vessel Reference is made to FIG. 4. illustrating pressure wave propagation in elastic vessel 100 filled by the fluid 101. Pressure changes cause local movements of the fluid 101 and vessel wall 102 in the form of a wave, so local velocity gradient (shear rate) 103 oscillate.

The rheological effect is directly relates to the share rate oscillations due to the oscillatory pressure gradient originated by the heart pulse. In oscillatory fluid movement, as blood moves back and forth in response to the oscillatory pressure gradient, the shear stress varies accordingly as a function of time given by:

$$T_s(t) = -\mu(S)\frac{\partial V(r,t)}{\partial r} \quad (1)$$

Where V(r,t) is velocity of shearing of upper layer relatively to the bottom layer, $$\frac{\partial V(r,t)}{\partial r}$$

is shear rate or velocity gradient along the vessel radius r (assuming each blood vessel is a straight circular cylindrical tube) and μ(S) is dynamically changing viscosity of the fluid through the structural variable S.

The shear stress is translated to shear rate or velocity gradient changes. Hence, each heart pulsation will be followed by the changes in axial and radial velocities gradients over all arterial vascular networks. In a system undergoing share rate oscillations, the coherent light is scattered by the moving RBC with axial and radial velocities distribution originated by a pulsatile driven pressure. The Brownian motion effect is negligible. The photo-detector placed in vicinity of the scatterers collects the speckled light which is further can be analyzed.

The shear rate depends on variety of rheological parameters, such as blood viscosity, vessels elasticity and the actual size of moving particles. The local axial velocity in oscillatory fluid movement can be derived by:

$$v(x,r,t) \approx V_{max}*(1-G*J_0(\zeta)/J_0(\Lambda))*f(t)$$

Where G is an elasticity factor, f(t) is a periodic function of heart beat frequency, $\zeta$ is a complex variable related to a radial coordinates and $\Lambda$ is a viscosity dependent variable. Taken the elasticity factor G=1 for the small vessels of radius R, the velocity radial profile v(r,t) can be described in cylindrical coordinates by the following relationship:

$$v(r,t) \approx v_{max}*(1-G*(r/R)^{\Xi})*f(t) \quad [2]$$

where −1<(r/R)<1, which is driven by systolic pressure wave and it is time phase-shifted with respect to the cardiac cycle, ξ represents the of blunting. For example, in 30 micron arterioles, there is a range of ξ 2.4-4 at normal flow rates. If ξ=2, a parabolic velocity distribution is obtained. Taken the elasticity factor for small vessels G=1, the rms velocity difference across the vessel can be calculated by:

$$\Delta V = v_{max} * F(t) \sqrt{\frac{\int dv(r) * r^2 * dr}{\int dv(r) * dr}} = \frac{\xi * R^2}{2+\xi} * v_{max} * f(t) \quad [3]$$

For small arterials (around 20 microns), the fluctuation of velocity from systolic to diastolic phases ranges from 1.5 mm/s to 2.5 mm/s. This results in a very significant fluctuation of standard deviation (rms) during the systolic-diastolic cycle. Any kind of response to the changes of shear stress can, therefore, be used for the heart rate derivation.

Figure 13:
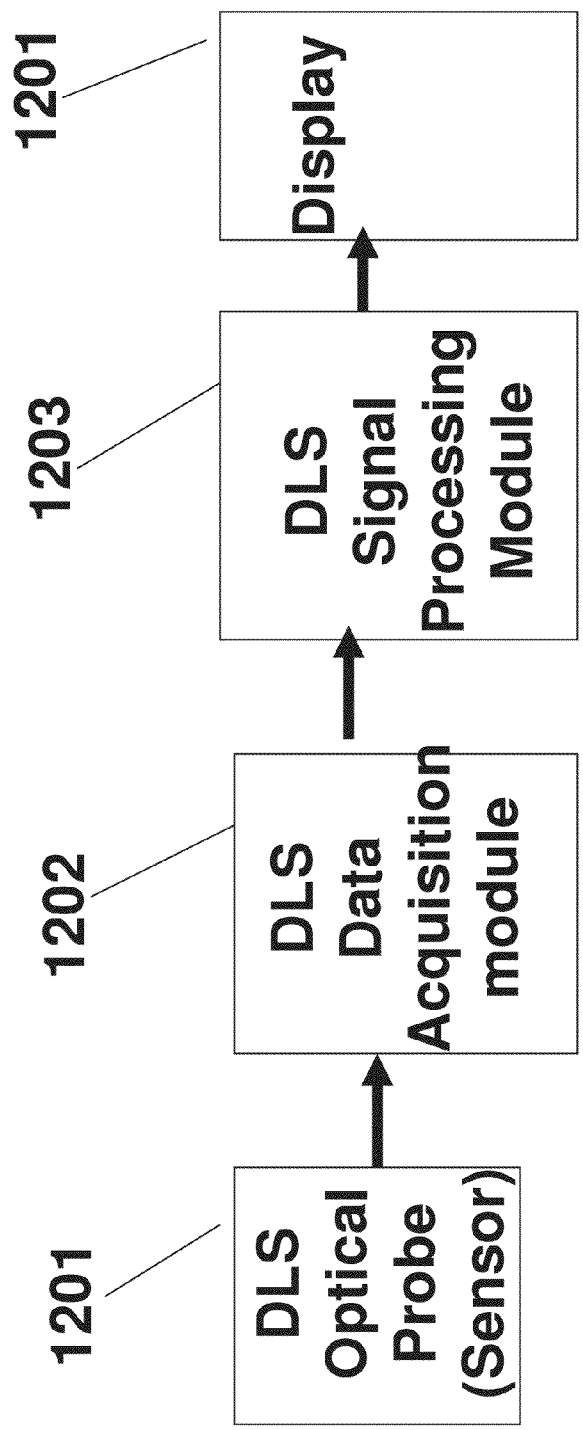

Reference is now made to FIG. 13 illustrating in a block diagram the major components of the DLS based physiological parameters measurement system 1200. The DLS system includes an optical probe 1201 containing visible or near-infrared light emitting element (e.g. laser) for generating at least partially coherent light, and a photodetector which produces an output current varying in accordance with the incident light. Detected DLS signal data are transmitted to acquisition module 1202, where they amplified and digitized for the further processing. Then the data are transmitted to signal processing module 1203. The signal processing module 1203 executes a heart rate and other needed physiological parameters calculation algorithm. The calculated physiological parameters are displayed on display 1204.

Figure 14:
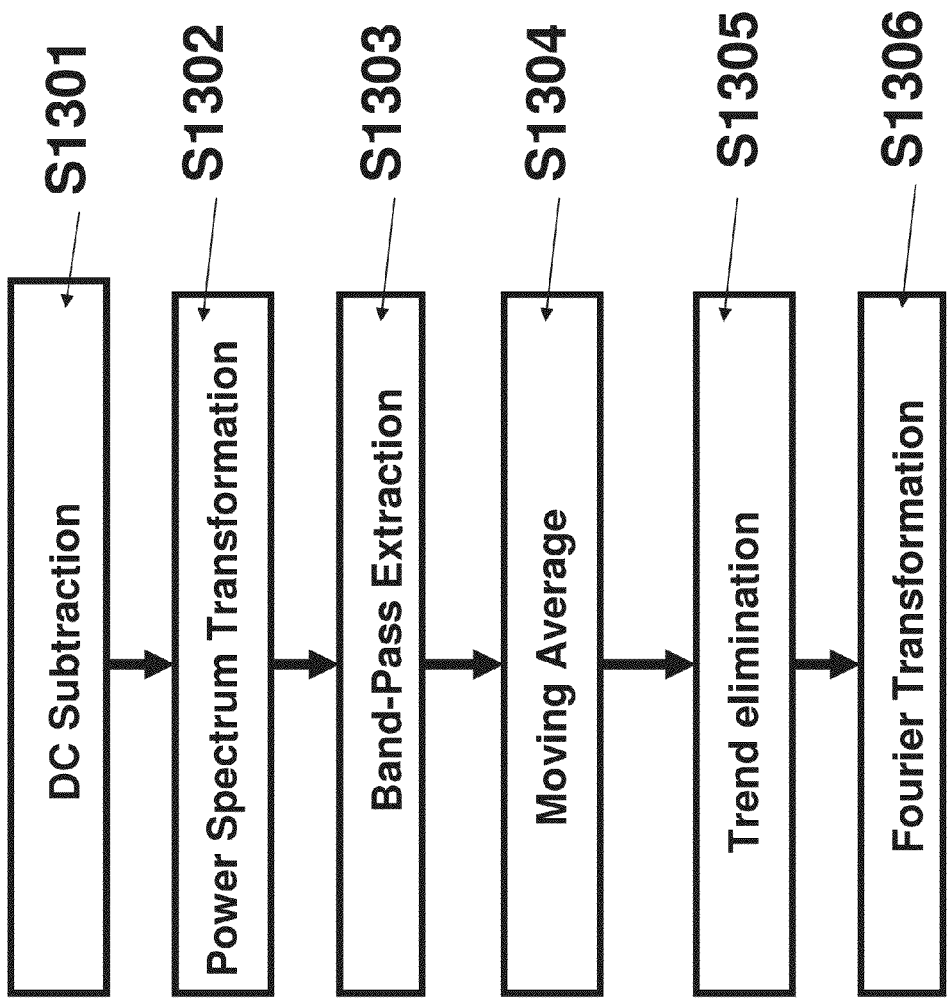
Figure 15A:
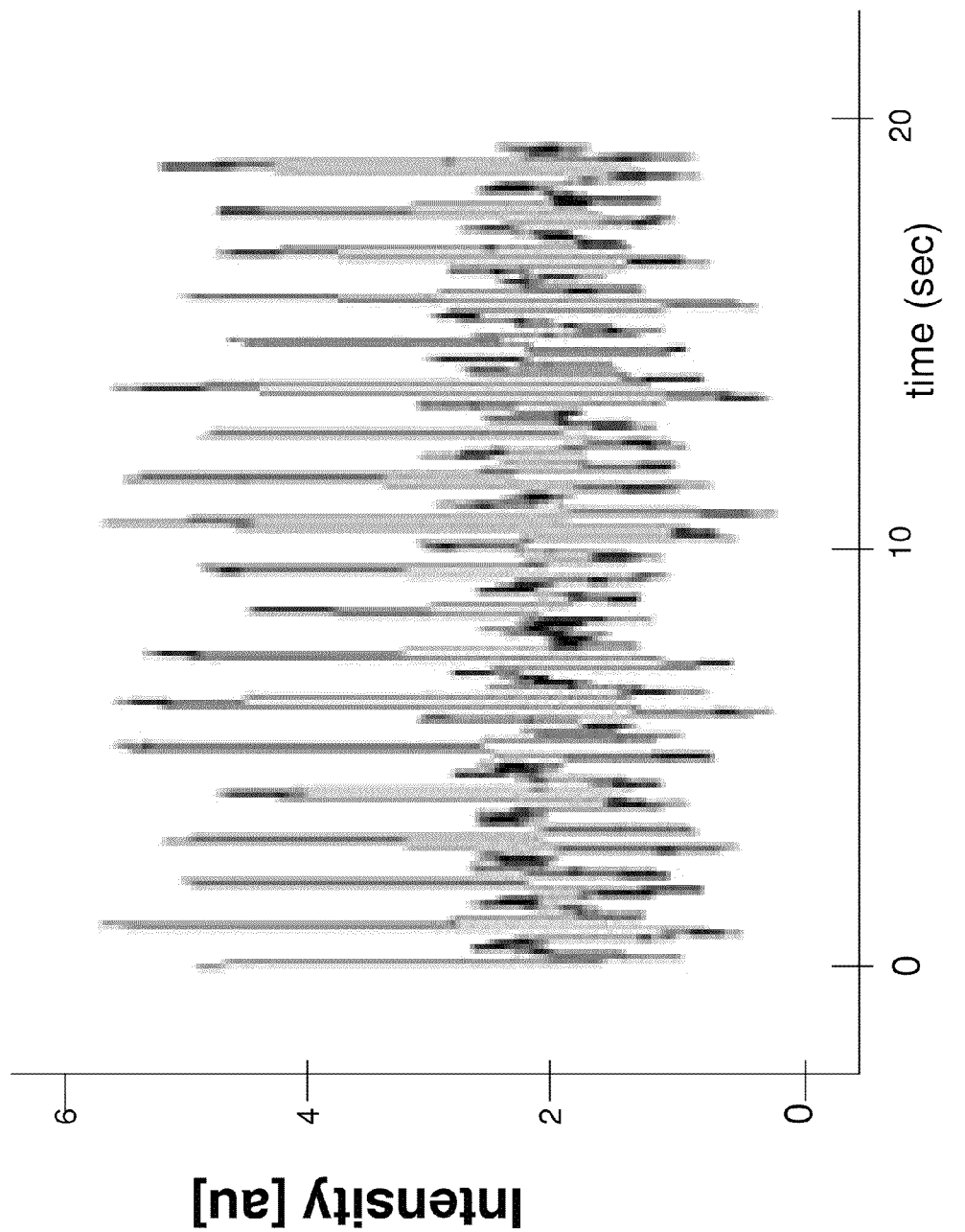
Figure 15B:
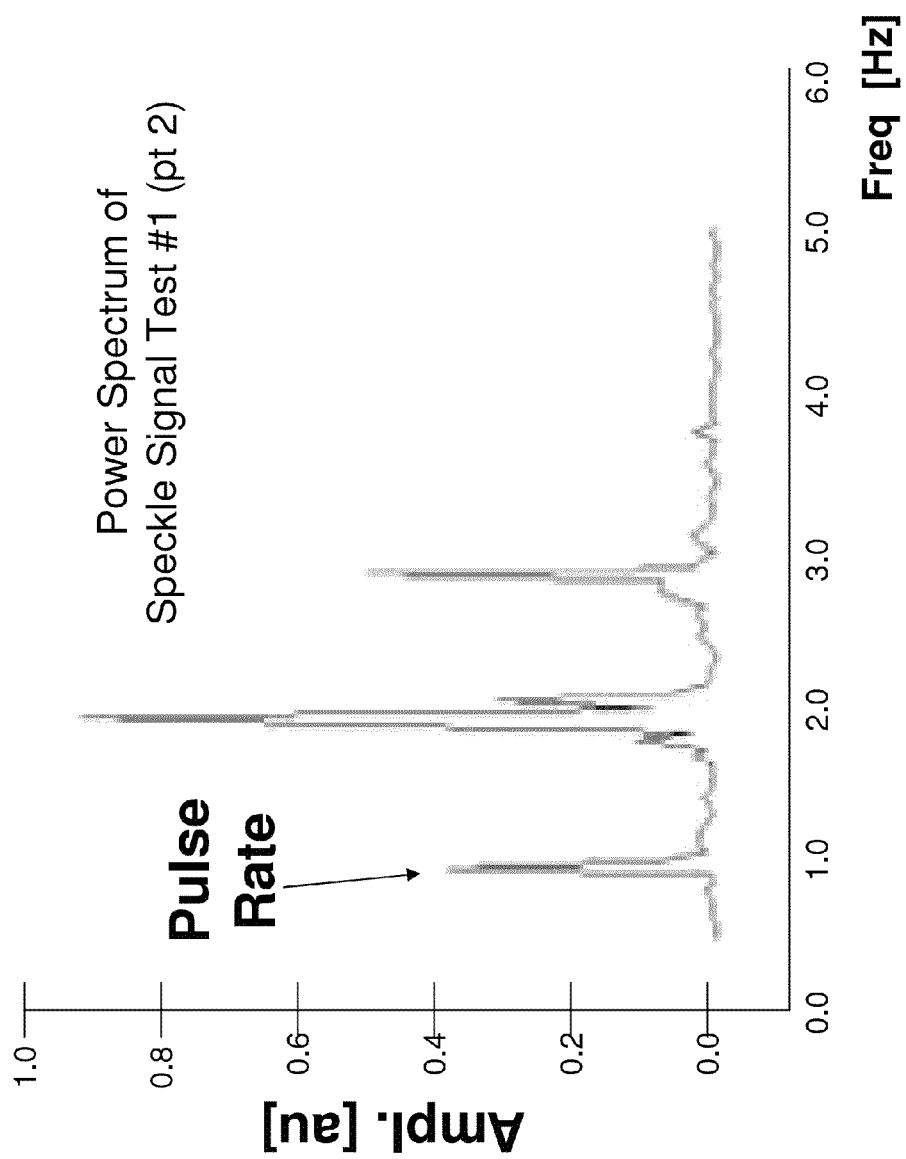
Figure 15C:
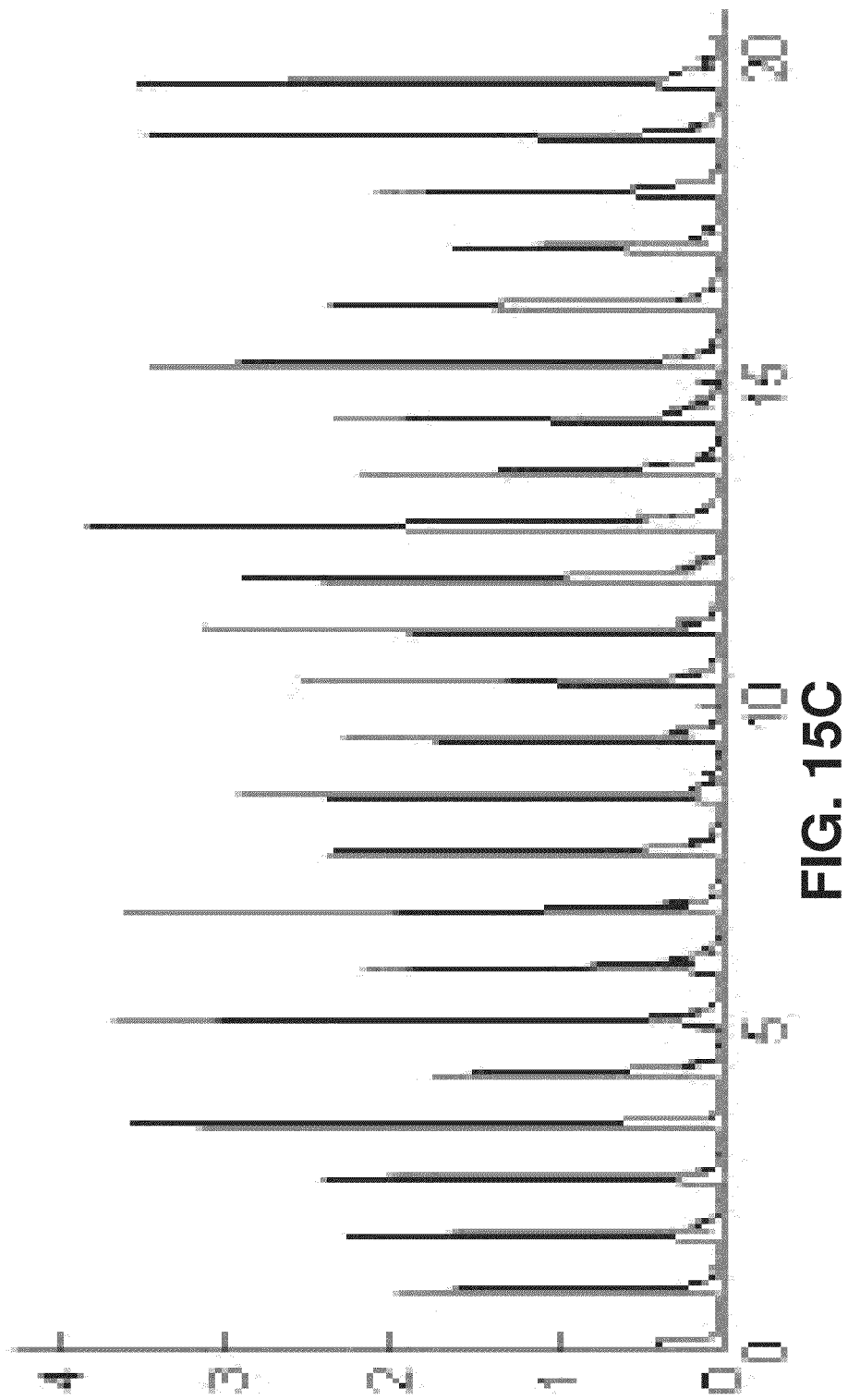
Figure 15D:
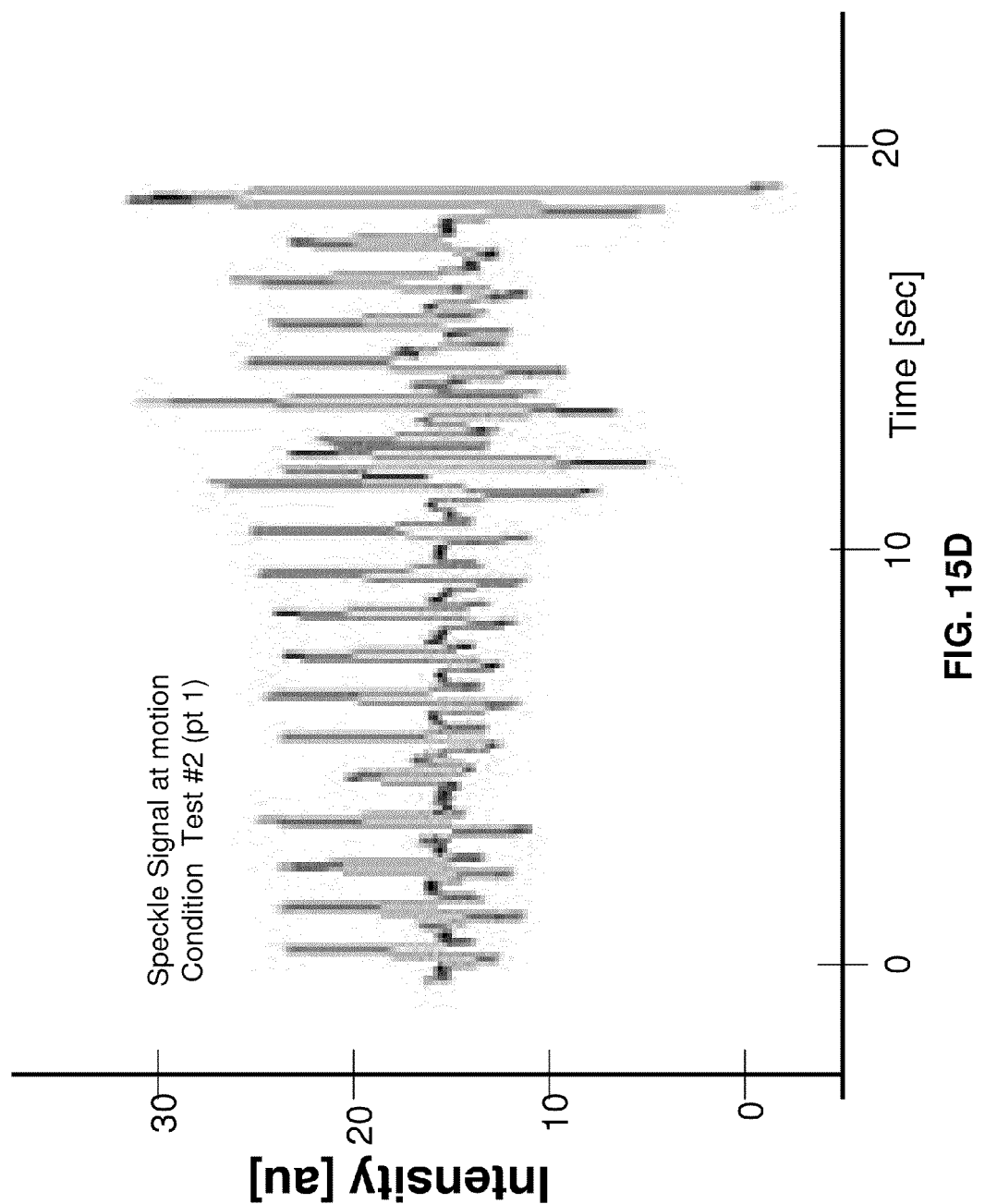
Figure 15F:
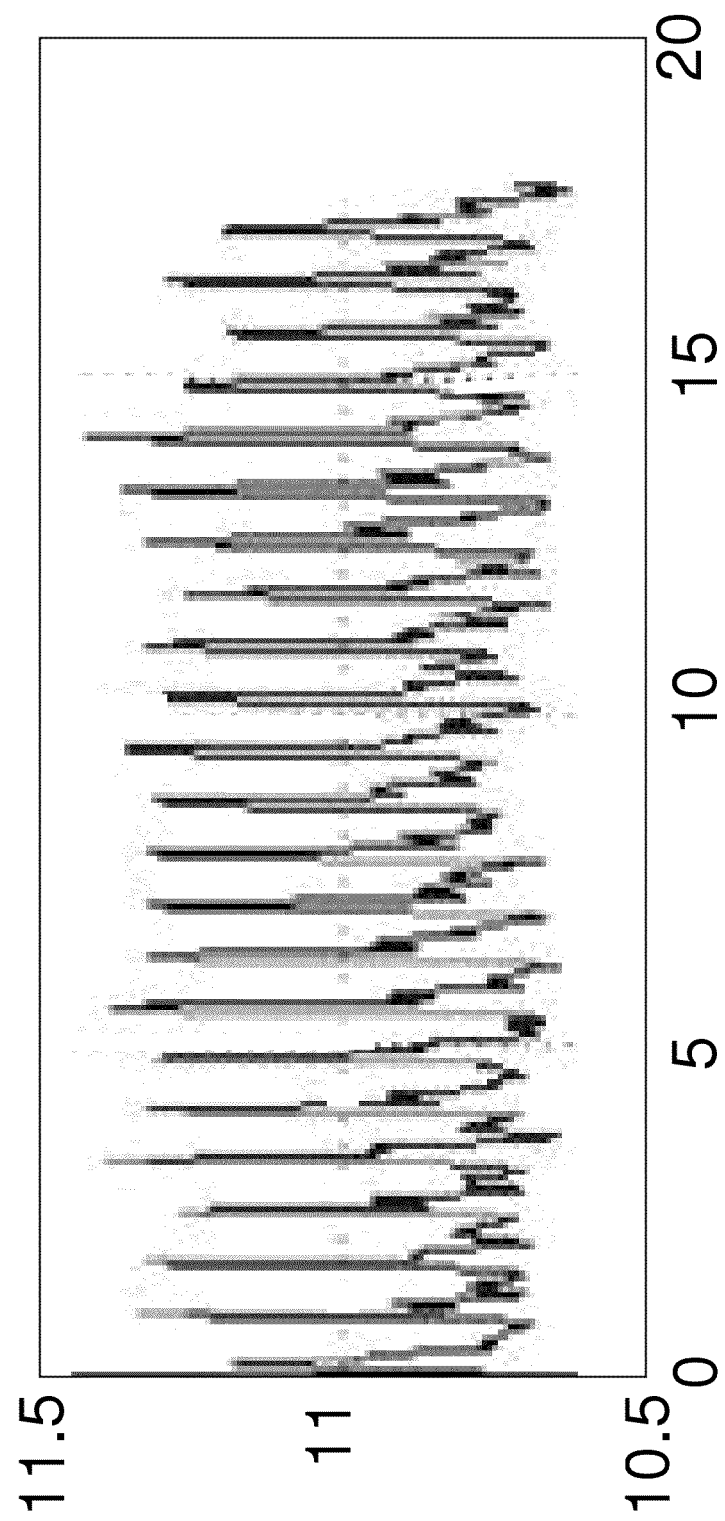

Reference is now made to FIG. 14 illustrating a simplified algorithm routine 1300 executed by the signal processing module 1203. The entered data undergoes DC component subtraction procedure 1301 followed by power spectrum transformation 1302. Power spectrum transformation allows further band-pass signal extraction 1303 in the frequencies interval (f1, f2) of the pulsatile signal along with the motion artifacts discrimination. Moving averaging procedure 1304 with further trend elimination procedure 305 enables clear pulsatile signal retrieving. Fourier transformation 1306 of the pulsatile signal results in the heart rate pattern.

The power spectrum of DLS ranges between 500 Hz and few kHz, thus the optical response to heart rate frequency is broadened because of shear rate velocities profile. Thus, the nature of the power spectrum processed using share stress approach to DLS signal is totally different from the PPG signal and trivial blood flow power spectrum. This enables to recognize, differentiate and further eliminate noise and motion artifacts.

In general, two standard approaches are commonly applicable to an analysis of DLS signals. The first approach uses the temporal autocorrelation of the intensity, and the second approach entails the analysis of the power spectrum P(w) of the detected signal. According to the first approach, the measured parameter is autocorrelation function $$g_1(\tau) = \frac{\langle E(0)E*(\tau)\rangle}{\langle |E(0)|^2\rangle}$$

which is related to the normalized filed correlate $$g_2(\tau) = \frac{\langle I(t)I(t+\tau)\rangle}{\langle I \rangle^2},$$

by $g_2(\tau)=1+\beta'|g_1(\tau)|^2$ that is well-known Siegert relation. Here β' is an adjustable parameter depending on the experimental conditions, I(t) is the intensity at time t and < ... > denotes an ensemble average For shear rate application the normalized field correlate approximation can be written as:

$$g_1(\tau) \approx \int_0^\infty P(V)\exp(-2k_0^2\langle \Delta V^2\rangle \tau^2) \cdot dV \quad (6)$$

where P(V,r) is an experimentally determined probability function, V is a velocity difference The measured autocorrelation function decay $\tau_c$ is governed by the velocity variations ΔV measured across the blood vessels. If V(r) is the standard deviation of velocity difference, then the decay time can be defined by:

$$\tau_c \approx \frac{1}{dV(r)} \quad [12]$$

According to the second approach, the power spectrum presentation is used to process the detected signal. The power spectrum of the measured signal can be constructed by using a standard Fast Fourier Transformation (FFT) digital signal processing algorithm. The total energy of a power spectrum PwS[f1,f2] is bounded in the frequencies interval (f1, f2) and can be evaluated by a simple summation. This value can be used as a measure of changes which occurs during any physiological processes.

FIG. 14 illustrates in steps S1301-S1306 various possible techniques that may be applied.

Reference is made to FIGS. 15A-15E illustrating examples of raw-data DLS signal with and without motion artifacts and its transformation into heart rate pattern. Signals shown in these examples are: a) motion artifacts free signal corresponding to shear rate oscillatory changes over 20 seconds period obtained from the DLS sensor; b) multi-stage frequency analysis showing dominant frequency corresponding to heart rate; c) processed signal corresponding to heart rate pattern; d) signal with motion artifacts corresponding to shear rate oscillatory changes over 20 seconds period obtained from the DLS sensor, e) multi-stage frequency analysis showing dominant frequency corresponding to heart rate; f) processed signal corresponding to heart rate pattern.

Reference is made to FIG. 15 illustrating in a simplified block diagram of the major components of the PPG oxyhemoglobin saturation measurement system synchronized by the DLS derived heart rate pattern. The system includes an optical sensor 501 containing visible or near-infrared light emitting element (e.g. laser) for generating at least partially coherent light, a PPG optical sensor 502 containing at list one visible and at least one near-infrared light sources and at list one photodetector which produces an output current varying in accordance with the incident light. Optical sensors 501 and 502 can be integrated on single board. Detected DLS signal data are transmitted to DLS signal acquisition module 503, where they amplified and digitized for the further processing. Then the data are transmitted to signal processing module 504. In one's turn, detected PPG signal is transmitted to PPG signal acquisition module 505, where they amplified and digitized for the further processing. The DLS signal processing module 504 executes heart rate pattern identification along with the motion artifacts discrimination. Using heart rate pattern the signal processing module 504 determines the timing for PPG signal processing executed by the PPG signal processing module 506. In addition, motion artifacts data identified by the DLS signal processing module 504 are also transferred to PPG signal processing module 506 for the motion artifacts subtraction and elimination procedure. Then, oxy-hemoglobin saturation parameters are displayed on display 507.

Also, extracted motion artifacts signal from the power spectrum is exploited for patient movements detection, which can be utilized together with oximeter like additional channel or being used as stand-alone device (actigraph).

Reference is made to FIG. 6 illustrating an example of wrist-mounted medical device and specifically the DLS-PPG sensor in more details. The DLS-PPG sensor is adjacent to an inner part of a wrist and includes at least two light emitting elements (e.g. lasers or LEDs) for generating at least partially coherent light; optical arrangement including focusing optics and possibly also collecting optics; and a detection unit (e.g. at least one photo diode). The electronic circuit that controls the illumination module (a driver) is located in a close proximity of the illumination module. The amplifier is located inside the enclosure of the DLS-PPG sensor to ensure that the electronic noise will be minimal. In a non-limiting example, one light emitting element may be a LED, and second light emitting element may be a laser diode or VCSEL (vertical cavity surface emitting laser). The light response i.e. the reflected light returned from the localized patient tissue region (patient's inner side of wrist in the present example) illuminated with the light emitting elements passes through an optical window and is collected by a detector (for example, one or more photo diodes) for the further processing by the processing unit.

Additional Discussion

Figure 7:
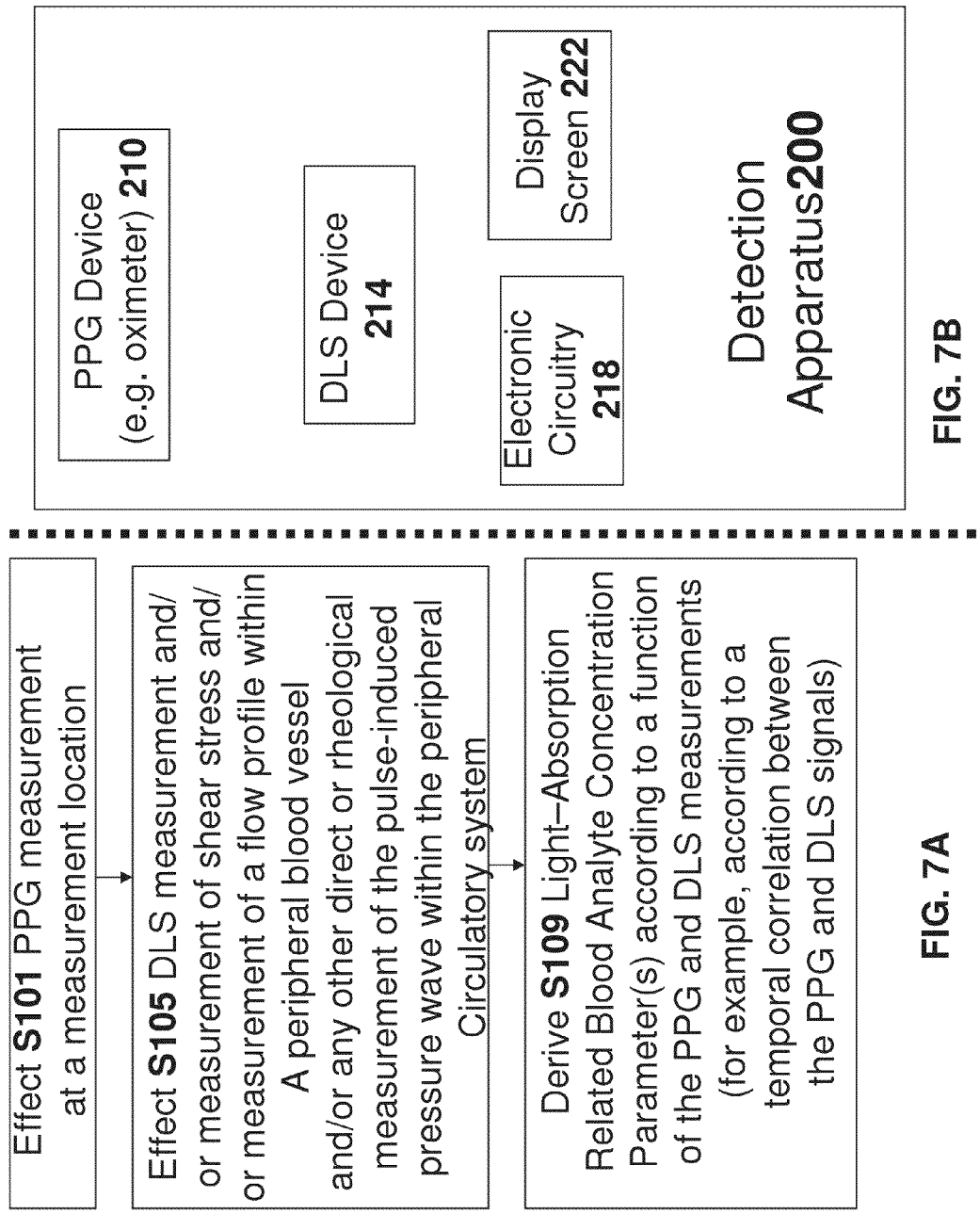
FIG. 7A-7B respectively illustrate a flow chart of a routine and a block diagram of an apparatus for measuring a blood oxygen saturation parameter according to PPG and DLS measurement in accordance with some embodiments.

FIG. 16 relates to FIG. 7 without of DLS—the additional wave-probing device may be used to effect a rheological pulse measurement.

Examples presented above related to electrical impedance measurements, acoustic measurements, optical (e.g. laser) or acoustical Doppler measurements, speckle measurements, frequency-shift measurements and any other rheological measurement of the pulse may be relevant for FIG. 16.

Electronic circuitry 218 or digital circuitry or any 'data processing unit' may include any software/computer readable code module and/or firmware and/or digital or analog hardware element(s) including but not limited to a CPU, volatile or non-volatile memory, field programmable logic array (FPLA) element(s), hard-wired logic element(s), field programmable gate array (FPGA) element(s), and application-specific integrated circuit (ASIC) element(s). Any instruction set architecture may be used in digital circuitry 280 including but not limited to reduced instruction set computer (RISC) architecture and/or complex instruction set computer (CISC) architecture.

All references cited herein are incorporated by reference in their entirety. Citation of a reference does not constitute an admission that the reference is prior art.

It is further noted that any of the embodiments described above may further include receiving, sending or storing instructions and/or data that implement the operations described above in conjunction with the figures upon a computer readable medium. Generally speaking, a computer readable medium may include storage media or memory media such as magnetic or flash or optical media, e.g. disk or CD-ROM, volatile or non-volatile media such as RAM, ROM, etc. as well as transmission media or signals such as electrical, electromagnetic or digital signals conveyed via a communication medium such as network and/or wireless links

Having thus described the foregoing exemplary embodiments it will be apparent to those skilled in the art that various equivalents, alterations, modifications, and improvements thereof are possible without departing from the scope and spirit of the claims as hereafter recited. In particular, different embodiments may include combinations of features other than those described herein. Accordingly, the claims are not limited to the foregoing discussion.

The invention claimed is:

1. A method of measuring one or more light-absorption related blood analyte concentration parameters of a mammalian subject, the method comprising:
 a) effecting a photoplethysmography (PPG) measurement of the subject by illuminating skin of the subject with at least two distinct wavelengths of light and determining relative absorbance at each of the wavelengths;
 b) effecting a dynamic light scattering measurement (DLS) of the subject to rheologically measure a pulse parameter of the subject;
 c) temporally correlating the results of the PPG and DLS measurements; and
 d) in accordance with the temporal correlation between the PPG and DLS measurements, assessing value(s) of the one or more light-absorption related blood analyte concentration parameter(s),
 wherein step (d) includes:
  i) computing a parameter descriptive of the temporal correlation between measurements of step (b) and step (c); and
  ii) in accordance with the computed temporal correlation parameter, determining a time-dependent PPG data quality value associated with each PPG measurement; and
  iii) computing the light-absorption related blood analyte concentration parameter(s) by assigning greater weight to PPG data having a higher data quality value and lesser or no weight to PPG data having a lower data quality value.

* * * * *